United States Patent [19]

Dugast-Zrihen et al.

[11] Patent Number: 5,616,798
[45] Date of Patent: Apr. 1, 1997

[54] POLY-IODINATED COMPOUNDS, PROCESS FOR THEIR PREPARATION, CONTRAST MEDIUM CONTAINING THEM

[75] Inventors: Maryse Dugast-Zrihen, Paris; Dominique Meyer, Saint Maur des Fosses, both of France

[73] Assignee: Guerbet S.A., Villepinte, France

[21] Appl. No.: 107,839

[22] PCT Filed: Feb. 25, 1992

[86] PCT No.: PCT/FR92/00172

§ 371 Date: Oct. 25, 1993

§ 102(e) Date: Oct. 25, 1993

[87] PCT Pub. No.: WO92/14695

PCT Pub. Date: Sep. 3, 1992

[30] Foreign Application Priority Data

Feb. 25, 1991 [FR] France .................................. 91 02226

[51] Int. Cl.⁶ ...................... C07C 233/03; C07C 233/04; C07C 233/05
[52] U.S. Cl. ........................................... 564/153; 564/152
[58] Field of Search ...................... 549/370, 369, 549/357; 424/5; 564/152, 153, 155, 158; 514/616

[56] References Cited

U.S. PATENT DOCUMENTS

| | | | |
|---|---|---|---|
| 4,102,924 | 7/1978 | Kalk et al. | 564/153 |
| 4,348,377 | 9/1982 | Felder et al. | 564/153 |
| 5,232,685 | 8/1993 | Speck et al. | 564/153 |

FOREIGN PATENT DOCUMENTS

| | | |
|---|---|---|
| 0118347 | 2/1984 | European Pat. Off. . |
| 0308364 | 9/1988 | European Pat. Off. . |
| 0357467 | 3/1990 | European Pat. Off. . |
| 3429949 | 2/1986 | Germany . |

*Primary Examiner*—Shailendra Kumar
*Attorney, Agent, or Firm*—Jacobson, Price, Holman & Stern, PLLC

[57] ABSTRACT

The invention relates to novel poly-iodinated compounds of general formula:

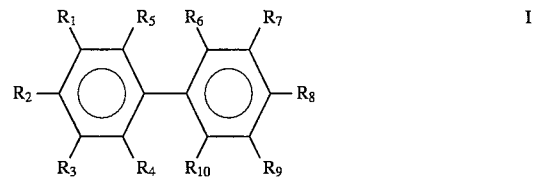

in which $R_1$, $R_2$, $R_3$, $R_4$, $R_5$, $R_6$, $R_7$, $R_8$, $R_9$ and $R_{10}$, identical or different, are selected from an iodine atom, a group of formula

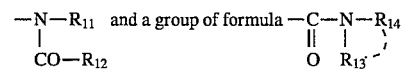

provided that at least two of the $R_1$, $R_2$, $R_3$, $R_4$, $R_5$, $R_6$, $R_7$, $R_8$, $R_9$ and $R_{10}$ groups represent an iodine atom, utilizable in contrast media for radiography. The invention also relates to a process for the preparation of these compounds as well as a contrast medium containing them.

7 Claims, No Drawings

POLY-IODINATED COMPOUNDS, PROCESS FOR THEIR PREPARATION, CONTRAST MEDIUM CONTAINING THEM

This application is a 371 of PCT/Fr 92/00172 filed Feb. 25, 1992.

The present invention relates to novel poly-iodinated compounds utilizable in contrast media for radiography.

The invention also relates to a process for the preparation of these compounds as well as the contrast media containing them.

The invention thus relates to poly-iodinated compounds of formula:

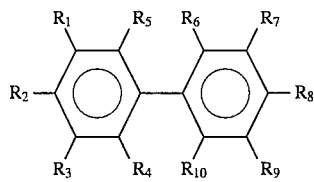

in which $R_1$, $R_2$, $R_3$, $R_4$, $R_5$, $R_6$, $R_7$, $R_8$, $R_9$, and $R_{10}$, identical or different, are selected from an iodine atom, a group of formula

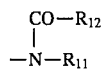

in which $R_{11}$ and $R_{12}$, identical or different, represent a hydrogen atom, a linear or branched $C_1$–$C_6$ alkyl group, a linear or branched $C_1$–$C_6$ hydroxy- or polyhydroxy-alkyl group, bearing optionally in addition one or more $C_1$–$C_6$ alkoxy groups, in particular methoxy or ethoxy, a linear or branched $C_1$–$C_6$ alkoxy - $C_1$–$C_6$ -alkyl group or a linear or branched $C_1$–$C_6$ hydroxy- or polyhydroxy-alkoxy —$C_1$–$C_6$- alkyl group bearing two to five —OH groups, a group of formula

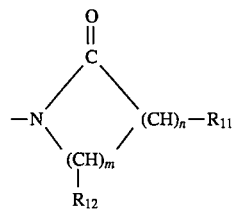

wherein $R_{11}$ and $R_{12}$ identical or different are as defined previously or represent hydroxy and n and m are integers selected so that the sum n+m is an integer from 3 to 6, a group $COO^-M^+$ or —COOH, $M^+$ representing a mineral or organic physiologically acceptable cation, a group of formula

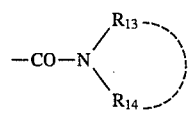

a group of formula

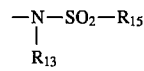

and a group of formula

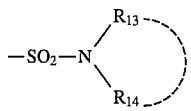

in which $R_{13}$ and $R_{14}$, identical or different, represent a hydrogen atom, a linear or branched $C_1$–$C_6$ alkyl group, a linear or branched $C_1$–$C_6$ hydroxy- or polyhydroxy-alkyl group, bearing optionally in addition one or more $C_1$–$C_6$ alkoxy groups, in particular methoxy or ethoxy, a linear or branched $C_1$–$C_6$ alkoxy $C_1$–$C_6$ -alkyl group or a linear or branched $C_1$–$C_6$ hydroxy- or polyhydroxy-alkoxy $C_1$–$C_6$ -alkyl group bearing two to five —OH groups, or $R_{13}$ and $R_{14}$ form together a $C_4$–$C_8$ alkylene, a $C_4$–$C_8$ hydroxy alkylene or a $C_4$–$C_8$ polyhydroxyalkylene group with a linear or branched chain, such that $R_{13}$ and $R_{14}$ form with the nitrogen atom to which they are attached a 5 or 6-membered nitrogenous heterocycle, optionally substituted by one or more hydroxy or $C_1$–$C_4$ hydroxyalkyl groups, and $R_{15}$ has the same meaning than $R_{13}$ excepted an hydrogen atom, provided that at least two of the $R_1$, $R_2$, $R_3$, $R_4$, $R_5$, $R_6$, $R_7$, $R_8$, $R_9$ and $R_{10}$ groups represent an iodine atom.

The invention is particularly concerned with poly-iodinated compounds of general formula I in which $R_1$, $R_2$, $R_3$, $R_4$, $R_5$, $R_6$, $R_7$, $R_8$, $R_9$ and $R_{10}$, identical or different, are selected from an iodine atom, a group of formula

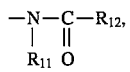

in which $R_{11}$ and $R_{12}$, identical or different represent a hydrogen atom, a linear or branched $C_1$–$C_6$ alkyl group, a linear or branched $C_1$–$C_6$ hydroxy- or polyhydroxyalkyl group, optionally bearing in addition one or more $C_1$–$C_6$ alkoxy groups, a linear or branched $C_1$–$C_6$ alkoxyalkyl group, or linear or branched $C_1$–$C_6$ hydroxy- or polyhydroxy- alkoxyalkyl group containing from two to five —OH groups, and a group of formula

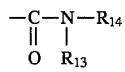

in which $R_{13}$ and $R_{14}$, identical or different, are as $R_{11}$ and $R_{12}$ defined above, provided that at least two of the $R_1$, $R_2$, $R_3$, $R_4$, $R_5$, $R_6$, $R_7$, $R_8$, $R_9$ and $R_{10}$ groups represent an iodine atom.

A first group of preferred compounds comprises the tetraiodinated compounds of general formula II:

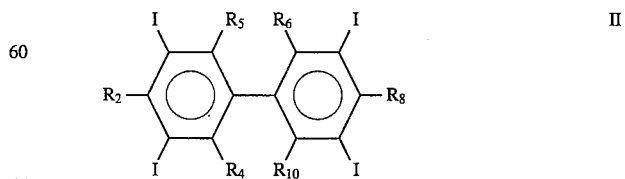

in which $R_2$, $R_4$, $R_5$, $R_6$, $R_8$ and $R_{10}$ are as defined previously.

A second group of preferred compounds comprises the hexaiodinated compounds of general formula III:

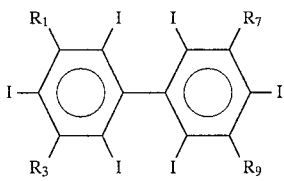

in which $R_1$, $R_3$, $R_7$ and $R_9$ are as defined previously.

The compounds of general formula I are preferred in which $R_{11}$, $R_{12}$, $R_{13}$ and $R_{14}$ are selected from: —H, —CH$_3$, —CH$_2$CH$_3$, —CH$_2$OH, —CHOH—CH$_3$, —CH(OCH$_3$)CH$_2$OH, —CHOH—CH$_2$(OCH$_3$),

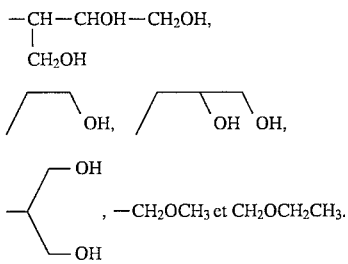

, —CH$_2$OCH$_3$ et CH$_2$OCH$_2$CH$_3$.

Preferred

—CO—N(R$_{13}$)(R$_{14}$)

groups are those in which:

—$R_{13}$ represents the

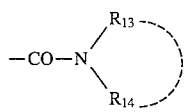

group and $R_{14}$ is selected from —H, —CH$_3$, —CH$_2$CH$_2$OH and —CH$_2$CHOH—CH$_2$OH;

—$R_{13}$ represents the

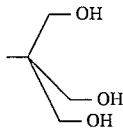

group, and $R_{14}$ is selected from —H, —CH$_3$, —CH$_2$CH$_2$OH and —CH$_2$CHOHCH$_2$OH;

—$R_{13}$ represents the

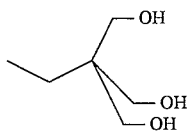

group and $R_{14}$ is selected from —H, —CH$_3$, —CH$_2$CH$_2$OH, —CH$_2$CHOHCH$_2$OH and —CH(CH$_2$OH)$_2$; —$R_{13}$ and $R_{14}$ form with the nitrogen atom to which they are attached a group

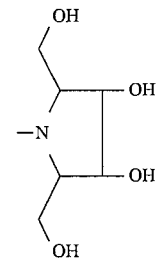

—$R_{13}$ represents a —CH$_2$CHOHCHOHCH$_2$OH group and $R_{14}$ is selected from —H, —CH$_3$, —CH$_2$CH$_2$OH, —CH$_2$CHOHCH$_2$OH and —CH(CH$_2$OH)$_2$;

—$R_{13}$ represents a

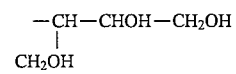

group, and $R_{14}$ is selected from —H, —CH$_3$, —CH$_2$CH$_2$OH, —CH$_2$CHOHCH$_2$OH and —CH(CH$_2$OH)$_2$.

Among the preferred

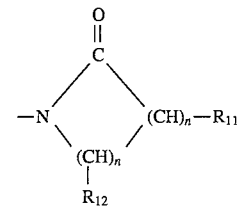

groups forming a heterocycle, the following groups may be cited:

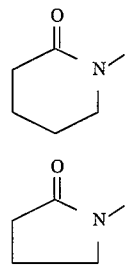

Among the tetra-iodinated compounds of general formula II, those are particularly preferred in which:

(I) $R_2$ and $R_8$ are identical and represent the

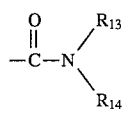

group and $R_4$, $R_5$, $R_6$ and $R_{10}$ are identical and represent the

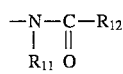

group.

(II) $R_2$ and $R_8$ are identical and represent the

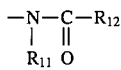

group and $R_4$, $R_5$, $R_6$ and $R_{10}$ are identical and represent the

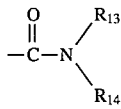

group.

(III) $R_2$, $R_5$, $R_6$ and $R_8$ are identical and represent the

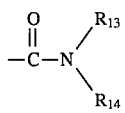

group and $R_4$ and $R_{10}$ are identical and represent the

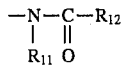

group, (IV) $R_2$, $R_4$, $R_5$, $R_6$, $R_8$ and $R_{10}$ are identical and represent the

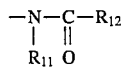

group;

$R_{11}$, $R_{12}$, $R_{13}$ and $R_{14}$ being as defined previously.

The preferred compounds of formula II are those in which:
- $R_2$ and $R_8$ represent the group —CO—NH—CH$_2$—CHOH—CH$_2$OH and $R_4$, $R_5$, $R_6$ and $R_{10}$ represent the —NH—CO—CHOH—CH$_3$ group (compound No. 4);
- $R_2$ and $R_8$ represent the group —NH—CO—CH$_2$OH and $R_4$, $R_5$, $R_6$ and $R_{10}$ represent the group —CO—NH—CH$_2$—CH$_2$OH (compound No. 2);
- $R_2$ and $R_8$ represent the group

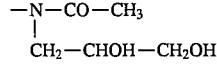

and $R_4$, $R_5$, $R_6$ and $R_{10}$ represent the group —CO—NH—CH$_2$—CH$_2$OH (compound No. 3);

$R_2$ and $R_8$ represent the group —NH—CO—CH$_2$OH and $R_4$, $R_5$, $R_6$ and $R_{10}$ represent the group —CO—NH—CH$_2$—CHOH—CH$_2$OH (compound No. 1);
- $R_2$, $R_5$, $R_6$ and $R_8$ represent the group —CO—NH—CH$_2$—CHOH—CH$_2$OH and $R_4$ and $R_{10}$ represent the group —NH—CO—CH$_2$OH (compound No. 7);
- $R_2$, $R_4$, $R_5$, $R_6$, $R_8$ and $R_{10}$ represent the group —NH—CO—CHOH—CH$_3$ (compound No. 5);
- $R_2$, $R_4$, $R_6$ and $R_8$ represent the group —CO—NH—CH$_2$—CH$_2$OH and $R_5$ and $R_{10}$ represent the group —NH—CO—CHOH—CH$_3$ (compound No. 6).

Among the hexa-iodinated compounds of general formula III, those are particularly preferred in which:

(V) $R_1$ and $R_7$ are identical and represent the group

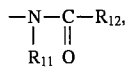

and $R_3$ and $R_9$ are identical and represent the group

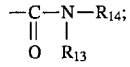

$R_{11}$, $R_{12}$, $R_{13}$ and $R_{14}$ being as defined previously;

(VI) $R_1$ and $R_9$ are identical and represent the group

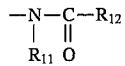

and $R_3$ and $R_7$ are identical and represent the group

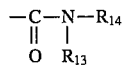

$R_{11}$, $R_{12}$, $R_{13}$ and $R_{14}$ being as defined previously;

(VII) $R_1$, $R_3$, $R_7$ and $R_9$ are identical and represent the group

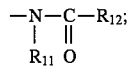

$R_{11}$ and $R_{12}$ being as defined previously;

(VIII) $R_1$, $R_3$ and $R_7$ are identical and represent the group

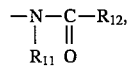

and $R_9$ represents the group

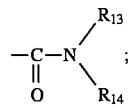

$R_{11}$, $R_{12}$, $R_{13}$ and $R_{14}$ being as defined previously.

(IX) $R_1$, $R_3$, $R_7$ and $R_9$ are identical and represent the group

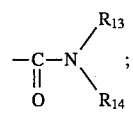

$R_{13}$ and $R_{14}$ being as defined previously.

The preferred compounds of formula III are those in which: —$R_1$ and $R_7$ represent the group —NH—CO—CH(CH$_2$OH)$_2$; and $R_3$ and $R_9$ represent the group

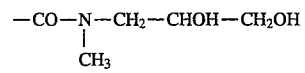

(compound No. 8)

—$R_1$ and $R_7$ represent the group —NH—CO—CH(CH$_2$OH)$_2$ and $R_3$ and $R_9$ represent the group —CO—N(CH$_2$—CHOH—CH$_2$OH)$_2$ (compound No. 9)

—$R_1$ and $R_7$ represent the group —NH—CO—$CH_2OH$ and $R_3$ and $R_9$ represent the group

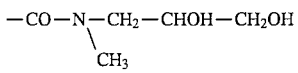

(compound No. 10),

—$R_1$ and $R_7$ represent the group —NH—CO—CHOH—$CH_2OH$ and $R_3$ and $R_9$ represent the group

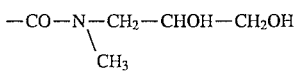

(compound No. 11),

—$R_1$ and $R_7$ represent the group —NH—CO—$CH_2OH$ and $R_3$ and $R_9$ represent the group

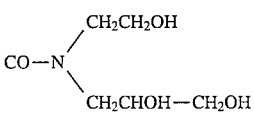

(compound No. 12),

—$R_1$ and $R_7$ represent the group

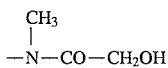

and $R_3$ and $R_9$ represent the group

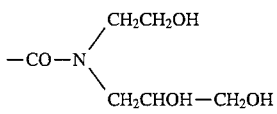

(compound No. 13),

—$R_1$ and $R_7$ represent the group —N—$(COCH_3)_2$ and $R_3$ and $R_9$ represent the group

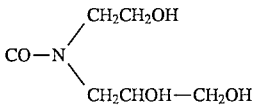

(compound No. 14)

—$R_1$ and $R_7$ represent the group

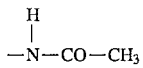

and $R_3$ and $R_9$ represent the group

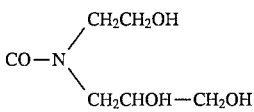

(compound No. 15),

—$R_1$ and $R_7$ represent the group

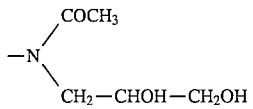

and $R_3$ and $R_9$ represent the group

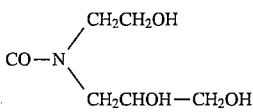

(compound No. 16).

The compounds of general formula I may be prepared by alkylation and/or acylation reactions.

The compounds of general formula I may be prepared in particular by a process comprising the following steps:

a) coupling of the benzene derivatives of formula IV and V

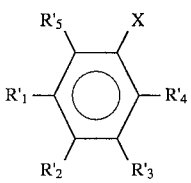

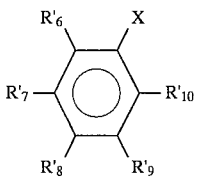

X being selected from chlorine, bromine and iodine and $R'_1$, $R'_2$, $R'_3$, $R'_4$, $R'_5$, $R'_6$, $R'_7$, $R'_8$, $R'_9$ and $R'_{10}$, identical or different, being selected from a hydrogen atom and the groups —$NO_2$ and —$CO_2R$ with R representing a $C_1$–$C_6$ alkyl group so as to obtain a compound of formula VI:

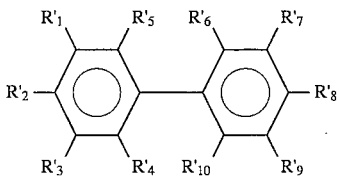

in which $R'_1$, $R'_2$, $R'_3$, $R'_4$, $R'_5$, $R'_6$, $R'_7$, $R'_8$, $R'_9$, $R'_{10}$ are as defined previously;

b) amidation of the —$CO_2R$ groups by an amine of formula

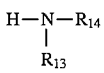

(XIII);

c) reduction of the nitro groups to amino groups;

d) iodination under standard conditions;

e) optional protection of the —OH groups by means of the usual protecting groups, f) acylation of the aromatic amino groups by an acid chloride of formula $R'_{12}$ —COCl; $R'_{12}$ representing a $R_{12}$ group as defined previously, the hydroxy groups of which are protected by means of a usual protecting group; and either g) optional alkylation of the amido groups by means of a reactant of formula Z—$R_{11}$, Z being a labile group such as Cl, Br or I and $R_{11}$ being as defined previously; and deprotection of the protected hydroxy groups, or h) deprotection of the protected hydroxy groups, and optional alkylation of the amino groups by a reactant of formula Z—$R_{11}$, $R_{11}$ being as defined previously.

The reaction of step a) preferably takes place in a suitable solvent such as xylene, nitrobenzene, nitrotoluene, DMF or pyridine, in the presence of a metal catalyst such as copper according to the method of ULLMAN (E. FANTA, Chem. Rev. 64, 613, 1964).

The reaction of step c) is a catalytic reduction by means of hydrogen on palladised charcoal or on Raney nickel or a chemical reduction.

The iodination reaction of step d) takes place under the usual conditions such as by means of aqueous ICl or $I_2$ in the presence of KI/ethylamine at temperatures included between 0° C. and 100° C.

The alkylation reactions of steps f) and g) are performed under standard conditions, in the presence of a strong base.

The compounds of formula II in which $R_2$, $R_4$, $R_5$, $R_6$, $R_8$ and $R_{10}$ represent a group

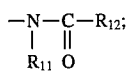

$R_{11}$ and $R_{12}$ being as defined previously, may also be obtained by a process consisting of the following steps:

a1) coupling of a benzene derivative of formula

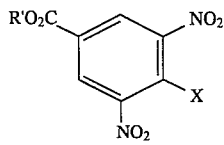

R' representing a methyl or ethyl group, and X being selected from chlorine, bromine or iodine atom following the ULLMAN reaction as described above in order to obtain a compound of formula VIII,

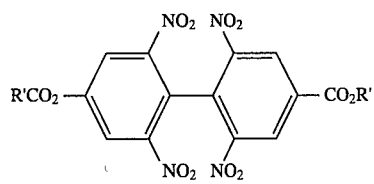

in which R' is as defined previously;

b1) after saponification of the esters, azide formation and rearrangement according to the SCHMIDT reaction to obtain a diamine of formula IX

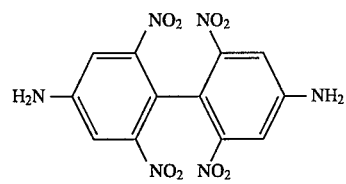

c1) acylation of the amino groups by means of an acid chloride of formula $R'_{12}$—COCl, $R'_{12}$ corresponding to $R_{12}$ as defined previously the —OH groups of which may or may not be protected.

d1) catalytic reduction or chemical reduction of the nitro groups to amino groups as described previously in step c).

e1) iodination of the aromatic amino groups as described previously in step d).

f1) acylation by means of an acid chloride of formula $R'_{12}$—$COC_1$, as described previously in f) R' being as defined previously.

g1) optional deprotection, and h1) optional alkylation as described previously in g).

The compounds of formula II may also be obtained by the HOFMANN rearrangement of the iodinated series, according to the method described in FR-A-84 15 494.

The compounds of formula II in which $R_2$, $R_4$, $R_5$, $R_6$, $R_8$ and $R_{10}$ represent the group

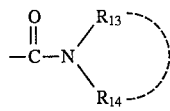

may be obtained in addition by standard processes according to which the aromatic $NH_2$ groups obtained in c) are converted into $CO_2H$ groups, by example by means of the SANDMEYER reaction in the iodinated series as described in the patent EP-A-32387.

The compounds of formula III in which $R_1$, $R_3$, $R_7$ and $R_9$ represent a group

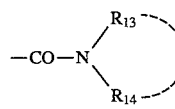

$R_{13}$ and $R_{14}$ being as defined previously, may be prepared by the following procedure:

a2) diazotation of a compound of formula:

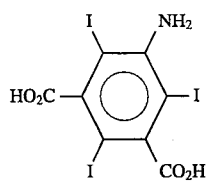

in order to obtain a compound of formula XI

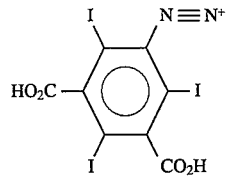

b2) coupling of the compound of formula XI in order to obtain a compound of formula XII

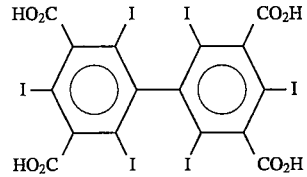

c2) conversion of the compound of formula XII into its corresponding acid chloride, and d2) amidation of the compound obtained with an amine of formula:

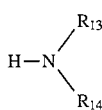

in order to obtain a compound of formula III in which $R_1$, $R_3$, $R_7$ and $R_9$ represent the group:

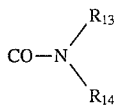

Compounds of formula III wherein $R_1$ and $R_7$ represent

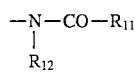

and $R_3$ and $R_9$ represent

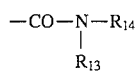

may additionally be obtained by a method consisting of the following steps:

coupling benzene derivatives of formula IV and V as previously defined so as to obtain a compound of formula VI bis:

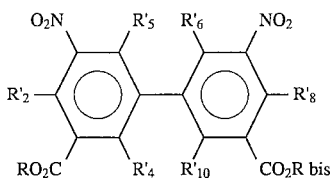

catalytic reduction of the nitro groups to amino groups as described previously, iodination as described previously, conversion of the COOR groups into acide chloride groups by means of a compound such as $SOCl_2$ or $(COCl)_2$ under standard conditions;

acylation of the amino groups by means of an acid chloride of formula $R'_{12}$—COCl as previously defined;

amidation of the —COCl groups by means of an amine of formula

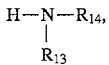

as previously defined;

deprotection of hydroxy groups which are protected;

optional alkylation of the amido groups by means of a reactant of formula Z—$R_{11}$, as previously defined.

The amines of general formula XII are for the most part known and commercially available compounds or may be prepared in the following manner.

The amine alcohol of formula:

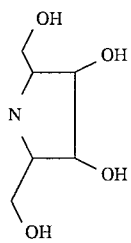

is prepared as described in Tetrahedron Letters, 31, 6777 (1990), J. Org. Chem., 50, 891 (1985) or J. Chem. Soc. Chem. Commun. 262 (1987).

The amine alcohol of formula XII in which $R_{13}$ represent H and $R_{14}$ represents

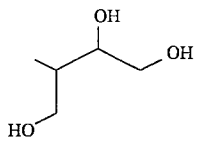

is prepared as described in U.S. Pat. Nos. 4,341,756 and 4,439,613.

The amine alcohol of formula XII in which $R_{13}$ represents —$CH_3$ and $R_{14}$ represents

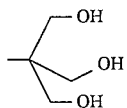

is prepared as described in Zh. Org. Khim., 22 (2), 298, 1986.

The amine-alcohol of formula XII in which $R_{13}$ represent —$CH_2CH_2OH$ and $R_{14}$ represents

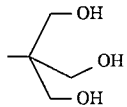

is marketed by Eastman Kodak.

The amine-alcohol of formula XII in which $R_{13}$ represents

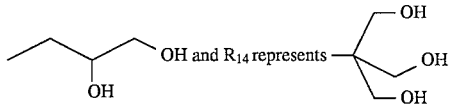

is prepared as described in J. Am. Chem. Soc. 66, 881, 1944.

The amine-alcohol of formula XII in which $R_{13}$ represents H, and $R_{14}$ represents

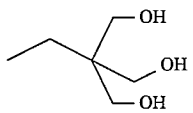

is prepared as described in Propellants, Explos., Pyrotech. 16(1), 40–42, 1991.

The amine-alcohols of general formula:

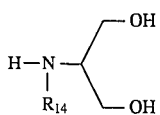

are prepared in the following manner:
when $R_{14}$ represents —$CH_3$, as described in EP-25083;
when $R_{14}$ represents —$CH_2CH_2OH$, as described in EP-25083 and J. Med. Chem. 10 (3), 511, 1967;
when $R_{14}$ represents

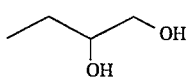

as described in J. Med. Chem. 10 (3), 511, 1967 and EP-25083.

The preparation of other amine-alcohols of formula XII will be described hereafter:

Preparation of compound No. 1

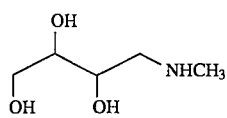

a) Preparation of the compound of formula

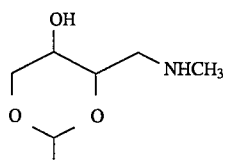

2 g (13.7 mmoles) of 2,4-ethylidene D-erythrose obtained according to the procedure described in J. Am. Chem. Soc. 2301, 1960 Barker R. et al. are dissolved in 10 ml of water at 30° C. 10 ml of a 40% aqueous solution of methylamine are added dropwise at 0° C. After the reaction mixture has warmed to room temperature, stirring is continued for 2 h. The solution is then reduced at room temperature in the presence of palladium on charcoal. The catalyst is then filtered off and the filtrate is concentrated to dryness. After solidification in ethyl ether, 1.7 g of the title compound are obtained, i.e. a yield of 77%. TLC (dioxan/$H_2O$/$NH_3$:8/3/2) Rf: 0.74 TLC ($CH_2Cl_2$ MeOH 8/2) Rf: 0.17.

$^{13}$C NMR (DMSO) (δ, ppm) 200 MHz 98.2 ($\underline{C}$—$CH_3$); 80.3 ($\underline{C}H$—O); 70.5 ($\underline{C}H_2$—O); 63.4 ($\underline{C}HOH$); 53.1 ($\underline{C}H_2$—N); 36.5 (NH—$\underline{C}H_3$); 20.7 (C—$\underline{C}H_3$).

b) Preparation of the compound of formula:

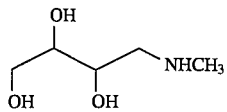

1.5 g (9.3 mmoles) of the compound obtained in a) are dissolved in 20 ml of 2N HCl. The solution is stirred at 50° C. for 5 h. After concentration and purification by passage through a H$^+$ resin, the solution is evaporated to dryness. The residue is taken up in ethyl ether. After filtration and drying, 0.8 g of the title compound are obtained (yield: 64%). TLC (dioxan/$H_2O$/$NH_3$:8/3/2) Rf: 0.18

$^{13}$C NMR (DMSO) (δ,ppm) 200 MHz 74.5 ($\underline{C}H$—$CH_2OH$); 69.6 ($CHO\underline{C}H_2$); 63.3 ($\underline{C}H_2OH$); 54.7($\underline{C}H_2$); 36.12 (NH$\underline{C}H_3$) MS (DCI(NH$_3$) m/z; 153 (M+ NH$_4^+$); 136 (M+H$^+$) base peak Preparation of the compound No. 2

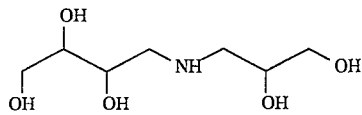

a) Preparation of the compound of formula:

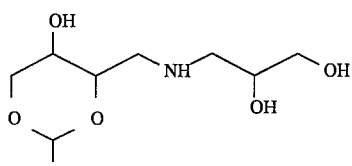

The compound is prepared according to the method described previously.

The reductive amination of 2,4-ethylidine-D-erythrose (6 g, 41 mmoles) is performed in the presence of aminopropanediol (1.2 equiv.) in ethanol (40 ml).

After chromatography on a column of silica, the title compound is obtained in a yield of 73%. TLC (dioxan/$H_2O$/$NH_3$:8/3/2) Rf: 0.73

$^{13}$CNMR (DMSO) δ, ppm (200 MHz)(98, $\underline{C}$—$CH_3$); (80.2–80.5, $\underline{C}H$—O); (70.2–70.4, $\underline{C}H_2$—O); (70.3, $\underline{C}HOH$); (64.5–64.6, $\underline{C}H_2OH$); 62.2–63.1, $\underline{C}H$—OH); (52.9–53, $\underline{C}H_2$); (50.8–51, $\underline{C}H_2$); (20.5, $\underline{C}H_3$).

b) Preparation of the compound of formula:

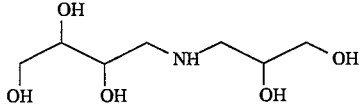

6 g (29.8 mmoles) of the compound obtained in the preceding step are deprotected by treatment with 5N HCl (50 ml). The reaction medium is stirred for 4 h at 50° C. After evaporation, the residue obtained is purified on a H$^+$ resin. After concentration and solidification in ethyl ether, 2.6 g of the title compound are obtained (yield 54.7%) TLC (dioxan/$H_2O$/$NH_3$:8/3/2) Rf: 0.39

$^{13}$C NMR (DMSO) (δ,ppm) 74.3 ($\underline{C}H$—$CH_2OH$) butanetriol chain); 70.3 ($\underline{C}HCH$—$CH_2$)×2; 64.5–64.6 ($\underline{C}H_2OH$ butanetriol chain); 63.3 ($\underline{C}H_2OH$); 52.8 ($CH_2N$)×2 MS (DCI/NH$_3$) m/z 196 (M+H$^+$) base peak; 178 (M+H$^+$—H$_2O$); 160 (M+H$^+$—2H$_2O$) 136, 122, 109, 92.

Preparation of the compound No. 3

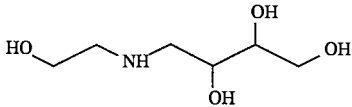

In the same manner as methylamine (for the preparation of the amino-alcohol No. 1) and aminopropanediol (for the preparation of the amino-alcohol No. 2) ethanolamine in the presence of 2,4-ethylidene-D-erythrose leads to the title compound under the same conditions of reductive amination.

a) Data of the compound of formula:

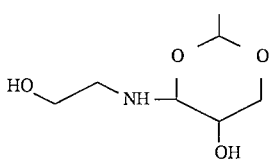

TLC (CH$_2$Cl$_2$/MeOH/NH$_3$: 8/2/1) Rf: 0.56

$^{13}$C NMR (DMSO) (δ, ppm) 97.9 (C—CH$_3$); 80.5 (CH—O); 70.2 (CH$_2$OH); 62.9 (CHOH); 60.2 (CH$_2$—O); 51.6 (CH$_2$—N); 50.7 (CH$_2$—N); 20.4 (CH$_3$).

b) Data of the compound of formula:

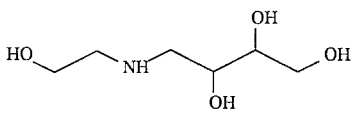

TLC (CH$_2$Cl$_2$/MeOH/NH$_3$ 55/30/15) Rf: 0.25 TLC (dioxan/H$_2$O/NH$_3$:8/3/2) Rf: 0.48

$^{13}$C NMR (DMSO) (δ, ppm) 74.5 (CHOHCH$_2$OH); 70.2 (CHOH—CH$_2$); 63.5 (CHOHCH$_2$OH); 60.4 (CH$_2$—CH$_2$OH); 52.5 (CH$_2$—CHOH); 51.8 (CH$_2$CH$_2$OH).

By employing- the procedures described previously and by using serinol with 2,4-ethylidene-D-erythrose, the amine-alcohol of the following formula is prepared in the same manner:

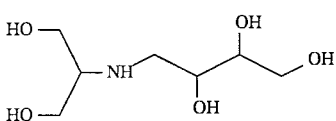

(compound No. 4)
Preparation of the compound No. 5

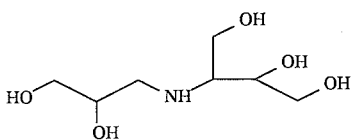

3 g (18 moles) of 2,3-epoxy 1,4-butanediol prepared according to the method described in J. Med. Chem. 1976, vol. 9, No. 1, 153–158 are dissolved in 10 ml of methanol. 0.9 equiv. of aminopropanediol in 10 ml of methanol are added dropwise at room temperature. The reaction mixture is heated at 45°–50° C. for 48 h. After evaporation, the crude product is purified on a H$^+$ resin and is concentrated to dryness. After being taken up in ether and dried, 4 g of the title compound are obtained (Yield 72.7%). TLC (dioxan/H$_2$O/NH$_3$:8/3/2) Rf : 0.58 TLC (CH$_2$Cl$_2$/MeOH/NH$_3$: 6/3/1) Rf : 0.55

$^{13}$C NMR (DMSO) (δ, ppm) 71–71.2 (CHOH); 64.6(—NH—CH—CH$_2$OH); 63.5 (CH$_2$OH propanediol chain); 61.4 (—CH—); 61 (CH$_2$OH); 51.3 (CH$_2$—N).

The opening of the epoxide previously described may also be carried out using methylamine, ethanolamine and serinol so as to obtain respectively the compounds:

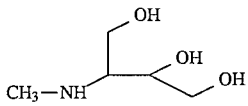

amine-alcohol No. 6

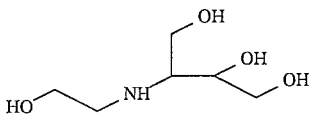

amine-alcohol No. 7

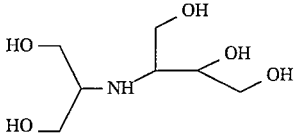

amine-alcohol No. 8

Preparation of the compound of formula:

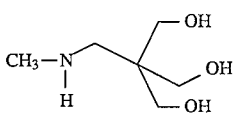

(amine-alcohol No. 9)

18.1 g (1 mmole) of 3-hydroxymethyloxetane prepared according to the method described in Propellants, Explos., Pyrotech., 16(1) 40–42, 1991 are stirred in 20 ml of methanol and 76 ml (1 mole) of 40% aqueous methylamine at 50° C. for 24 h. The mixture is evaporated to dryness and the residue is dissolved in 100 ml of 0.1N sulfuric acid.

The solution is refluxed for 12 h, then passed through a resin. The title compound is obtained by evaporation of the eluent.

Preparation of the compound of formula:

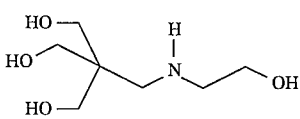

(amine-alcohol No. 10)

18.1 g (0.1mole) of 3-bromo ethyl-3-hydroxymethyloxetane obtained as described previously are stirred in 20 ml of methanol and 60.5 ml (0.1 mole) of ethanolamine at 50° C. for 24 h. The mixture is evaporated to dryness and the residue is dissolved in 100 ml of 0.1N sulfuric acid. The solution is refluxed for 12 h then passed through a resin. The title compound is obtained by evaporation of the eluent.

It will be obvious that the invention encompasses not only the compounds of formula I in the form of racemic mixtures but also the stereoisomers such as enantiomers, diastereoisomers, atropoisomers, SYN-ANTI isomers, ENDO-EXO isomers, E-Z isomers, associated with the presence of asymmetric carbon atoms and/or with restriction of rotation due to the steric hindrance created by the iodine atoms and/or by the substituents R$_1$ to R$_{10}$ of the compounds of formula I.

The present invention also relates to contrast media which contain at least one compound of formula I.

These contrast media are used in man and animals for radiological purposes.

The preferred pharmaceutical form of the contrast media according to the invention consists of aqueous solutions of the compounds. According to one embodiment of the invention, the compounds are encapsulated within liposomes.

The aqueous solutions usually contain a total of 5 to 100 g of compounds per 100 ml and the injectable volume of such solutions may vary generally from 1 to 1000 ml. The solutions may also contain additives such as a sodium salt, in particular sodium citrate, heparin and disodium-calcium EDTA.

These compositions may be administered by all of the routes commonly used for iodinated non-ionic contrast media. Thus, they may be administered by the enteral or parenteral routes (intravenous route, intraarterial route, opacification of the cavities) and, in particular, into the subarachnoidal space.

Examples of the preparation of compounds according to the invention will be given hereafter.

EXAMPLE 1

Preparation of 4,4'-di-(hydroxyacetylamino)-2,2', 6,6'-tetrakis-(2,3-dihydroxypropylcarbamoyl) 3,3', 5,5'-tetraiodo diphenyl (compound No. 1).

1) Preparation of 2-bromo isophthalic acid 125 g (0.676 mole) of 2-bromo meta xylene are added rapidly to a solution of 440 g (4.1×0.676 mole) of potassium permanganate in 2.5 l of water. After being refluxed with stirring for 48 h and allowed to cool to room temperature, the reaction mixture is filtered through Celite; after the cake has been washed with hot water, the volume of the filtrate is reduced to 1.5 l by evaporation. After being cooled to 0° C. the solution is acidified by means of 100 ml of 10N HCl to pH=1. The precipitate is filtered off, washed with water then dried for 12 h at 70° C. The product is obtained in a yield of 70.6% (117 g).

M.p.=222° Thin layer chromatography (TLC) (isopropanol/ethyl acetate (AcOEt)/NH$_4$OH: 25/25/30); R$_f$=0.25 TLC (toluene/methyl-ethyl-ketone/HCOOH:60/25/5): R$_f$:0.5 Determination of the acidity ((t-butyl)$_4$—N—OH 103.1% (1st acid function) 100.6% (2nd acid function).

2) Preparation of 2-bromo 5-nitro isophthalic acid

To a solution of 117 g (0.477 mole) of the preceding compound in 892 ml of 98% H$_2$SO$_4$ is added dropwise a mixture of fuming HNO$_3$ (167 ml) and concentrated H$_2$SO$_4$ (264 ml) while the temperature is maintained below 15° C. The reaction mixture is stirred for 12 h at room temperature. The precipitate is filtered off, washed with 3×200 ml of water, then dried at 70° C. for 12 h.

Yield 93.4%

M.p.=214° C. TLC (isopropanol 25/AcOEt 25/NH$_4$OH/ 30): R$_f$=0.45

$^1$H NMR (DMSO) 8.5 (s 2H arom) 13 (s, COOH 2H)

3) Preparation of the dimethyl ester of 2-bromo 5-nitro isophthalic acid 880 ml of methanol containing 129 g (0.445 mole) of the preceding compound and 90 ml of 98% H$_2$SO$_4$ are refluxed for 24 h. The precipitate obtained is filtered off, washed with 120 ml of methanol, then 2×120 ml of H$_2$O. After being dried at 65° C., the product is obtained in a yield of 74%.

M.p. 134° C. TLC (toluene 60/methyl-ethyl-ketone 35/HCOOH 25): R$_f$=0.8

IR 1730 (COOCH$_3$) 1350–1560 (NO$_2$)

NMR $^1$H DMSO 4.0 (s COOCH$_3$ 6H) 8.5 (s 2H arom)

4) Preparation of 4,4'-dinitro-2,2', 6,6-tetra(methoxy-carbonyl) diphenyl

To a solution of 100 g (0.314 mole) of the preceding product in 420 ml of p-xylene previously heated to 80° C. are added portionwise 36.0 g (0.566 mole) of copper. After 5 h of reflux (at 140° C.) a further 18 g (0.283 mole) of copper are added to the reaction mixture. The same operation is repeated after 12 h of reflux. The mixture is then filtered through Celite after a further 12 h period of reflux. In order to remove the CuBr which precipitates with the desired product, an extraction with CH$_2$Cl$_2$ is carried out; the filtrate is evaporated to dryness, taken up in ether, filtered then dried at 80° C. to give compound 5 in a yield of 70%

M.p.=226° C. TLC (CH$_2$C$_{12}$): R$_f$=0.1

$^1$H NMR (CDCl$_3$) 3.6 (s, COOCH$_3$ 12H) 9.0 (s 4H arom)

5) Preparation of 4,4'-dinitro-2,2', 6,6'-tetrakis-(2,3-dihydroxypropyl carbamoyl) diphenyl To 89.0 g of 2,3-aminopropanediol diluted in 450 ml of MeOH heated to 40° C., 49 g (0.103 mole) of the preceding product are added portionwise. After vigorous stirring for ½ h at 40° C., a quantity of MeONa sufficient to produce a homogeneous solution is added. After 12 h at room temperature, the mixture is evaporated and the residue is taken up in 1 l of H$_2$O and passed through columns of H$^+$ and OH$^-$ ion exchange resins. After evaporation to dryness, the product is crystallized from isopropanol, filtered off, washed with 2×250 ml of ether, then dried at 70° C. Yield 88.3%. TLC (Dioxan 9/H$_2$O 1) R$_f$=0.70

$^1$H NMR (DMSO) 2.8–3.2 (CH aliphatic 20H) 3.9–4.5 (OH 8 H exchangeable) 8.2 (s 4H aromatic) 8.3–8.6 (CON$\underline{H}$) 4H exchangeable).

6) Preparation of 4,4'-diamino 2,2', 6,6'-tetrakis-(2,3-dihydroxypropyl carbamoyl) diphenyl.

39 g (0.0550 mole) of the preceding product dissolved in 675 ml of H$_2$O in the presence of 13.4 g of 10% palladised charcoal are stirred under a H$_2$ pressure of about 3.10$^5$PA at room temperature for 6 hours.

After filtration of the catalyst and evaporation of the water, the residue is suspended in ethyl ether, filtered off, washed with 2×100 ml of ether and the product is dried in a vacuum at room temperature.

Yield=96.3% TLC (MeOH 8/CH$_2$Cl$_2$2) R$_f$=0.5 Determination of acidity (HClO$_4$) 93.5% per NH$_2$ function $^1$H NMR (DMSO) 2.7–4 (multiplet 20H aliphatic) 4.1–6 (multiplet 8H, OH; 4H NH$_2$ exchangeable) 6.7 (s 4H arom) 8.1–8.6 (m CON$\underline{H}$4H exchangeable)

Preparation of 4,4'-diamino-2,2', 6,6'-tetrakis-(2,3-dihydroxypropyl carbamoyl) 3,3', 5,5'-tetraiodo diphenyl 90.5 ml of 70% ICl are added dropwise to a solution of 54.5 g (0.0826 mole) of the preceding product in 545 ml of water. After heating to 80° C. for 8 h followed by stirring for 24 h at room temperature, the precipitate obtained is filtered of, washed with 20 ml of bisulfite and then with 40 ml of H$_2$O.

The first crop is obtained in a yield of 23.4% and a HPLC purity of 88%.

The recovery of a second crop is achieved by neutralization of the mother liquors to pH 5 with 5N sodium hydroxide. The I$_2$ precipitate is filtered off, the solution is evaporated to dryness and the residue is taken up in ethanol. The suspension obtained is filtered, washed with 2×200 ml of ethanol, followed by 200 ml of ether. After drying at 70° C., 103.5 g of product are obtained containing 50.7% by weight of NaCl. After purification by means of preparative HPLC on SiO$_2$ RP 18, the product is obtained in a purity with respect to iodine of 98.35%. Yield: 75% TLC (dioxan 9/H$_2$O 1/NH$_4$OH 1): R$_f$=0.45

$^1$H NMR (DMSO d$^6$) 2.7–3.7 (m 20H aliphatic) 4–6 (multiplets 8H OH; 4H NH$_2$ exchangeable) 8–8,8 (m, CONH 4H exchangeable).

8) Preparation of 4,4'-di-(acetoxyacetylamino) 2,2', 6,6'-tetrakis-(2,3-di-acetoacetoxypropyl carbamoyl) 3,3', 5,5'-tetraiodo diphenyl.

To a solution of 40.6 g (0.0351 mole) of the preceding product in 320 ml of anhydrous DMAC are added 71.9 g (15×0.0351 mole) of acetylated glycolic acid chloride. The temperature of the reaction mixture is heated to 58° C., then the solution is stirred vigorously for 12 h at 50° C. The residue is taken up in 500 ml of CH$_2$Cl$_2$ and washed with water. The organic phase is dried over Na$_2$SO$_4$, filtered and the volume is reduced by ¾ to permit precipitation with ether. The suspension obtained is filtered and the precipitate is washed with 2×200 ml of ether.

Yield: 100%; amine test negative.

$^1$H NMR DMSO 2.0–2.3 (s OCOCH$_3$ 30H) 4.0–5.5 (m 40H aliphatic) 8.3–9.0 (m CONH, 4H exchangeable) 10.2–10.4 (m NHCO 2H exchangeable)

9) Preparation of 4,4'-di-(hydroxy-acetylamino) 2,2', 6,6'-tetrakis-(2,3-dihydroxypropyl carbamoyl) 3,3', 5,5'-tetraiodo diphenyl (compound No. 1

75.7 g (0.0351 mole) of the preceding product are dissolved in 1.1 l of NaOH. After being stirred for 1 h 30 at room temperature, the reaction mixture is diluted with 700 ml of H$_2$O for passage through H$^+$ and OH$^-$ ion exchange resins. The solution obtained at pH 7.2 is evaporated.

Compound No. 1 is obtained in a yield of 60.2%. TLC (dioxan 9/H$_2$O 1/NH$_4$OH 2): R$_f$=0.4 Purity with respect to iodine: 99.29% HPLC purity=99.3% in 2 isomeric peaks (C8 Hypersyl 5M.15 cm buffer NaH$_2$PO$_4$/MeOH 92/8.

$^1$H NMR (DMSO) 2.6–6 (m. complex 24H aliphatic 10H OH exchangeable) 8–8.8 (m. CONH 4H exchangeable) 9.8–10.4 (m, NHCO, 2H exchangeable).

EXAMPLE 2

Preparation of 4,4'-di-(hydroxy-acetylamino)-2,2', 6,6'-tetra-(2-hydroxyethyl carbamoyl) 3,3', 5,5'-tetraiodo diphenyl (compound No. 2)

1) Preparation of 4,4'-dinitro 2,2', 6,6'-tetra (2-hydroxyethyl carbamoyl) diphenyl 4,4'-dinitro-2,2', 6,6'-tetramethoxycarbonyl diphenyl is prepared as indicated in part 4 of the preceding example.

35 g of the product obtained is then added portionwise to a solution of ethanolamine (42.6 g) in 350 ml of MeOH at 40° C. After vigorous stirring for ½ h at 40° C., powdered MeONa is added until a homogeneous solution is obtained.

The reaction mixture is stirred for 12 h at 40° C., evaporated, taken up in 700 ml of water then passed through H$^+$ and OH$^-$ ion exchange resins. After evaporation to dryness, the product is crystallized from acetone. It is filtered off, washed with ether and dried at 70° C. The product is obtained is a yield of 78.2%. TLC (CH$_2$Cl$_2$ 8/MeOH 2) R$_f$=0.75

$^1$H NMR (DMSO) 2.9–3.5 (m. 16H aliphatic) 3.6–4.8 (m OH 4H exchangeable) 8.1–8.3 (s 4H arom) 8.4–8.8 (m CONH 4H exchangeable with D$_2$O)

2) Preparation of 4,4'-diamino-2,2', 6,6'-tetra-(2-hydroxyethyl carbamoyl) diphenyl 34 g of the preceding product are dissolved in 900 ml of H$_2$O and in the presence of 10.5 g of 10% palladised charcoal are subjected to H$_2$ pressure of 3.10$^5$ Pa with stirring at room temperature for 6 h. After filtration of the catalyst, the water is evaporated to give a final volume of 350 ml which is used as such in the next step. TLC (MeOH 8/CH$_2$Cl$_2$ 2): R$_f$=0.55 (product not isolated)

3) Preparation of the 4,4'-diamino-2,2', 6,6'-tetra-(2-hydroxyethyl carbamoyl) 3,', 5,5'-tetraiodo diphenyl 50 ml of 70% ICl are added dropwise to the solution of the product obtained in the preceding step. After heating the reaction mixture at 80° C. for 3 h, the suspension obtained is filtered and washed with bisulfite and then abundantly with water. After being dried in a vacuum at 60° C. for 24 h, the desired product is obtained in a yield of 82.3%. TLC (CHCl$_2$ 8/MeOH 2) R$_f$=0.7

$^1$H NMR (DMSO) 2.9–3.5 (m 16 aliphatic) 3.8–5 (m 4H, OH and 4H, NH$_2$ exchangeable with D$_2$O) 8.2–8.7 (m 4H CONH exchangeable)

4) Preparation of 4,4'di-(acetoxyacetylamino) 2,2', 6,6'-tetra-(acetoxy-acetoxy carbamoyl) 3,3', 5,5'-tetraiodo diphenyl 101.2 g (12×0.0618 moles) of acetylated glycolic acid chloride are added rapidly to a solution of 64 g (0.0618 mole) of the preceding product in 1.1 l of anhydrous DMAC. After being heated for 12 h at 60° C., the mixture is evaporated, the residue is extracted with 700 ml of CH$_2$Cl$_2$ and washed with 250 ml of H$_2$O. After drying of the organic phase over MgSO$_4$ and filtration, the filtrate is treated with active charcoal. After evaporation, the residue is crystallized from ether. After being dried in a vacuum, the desired product is obtained in a yield of 88.5%. TLC (CH$_2$Cl$_2$ 9/MeOH 1): R$_f$=0.95 Purity with respect to iodine 99.4%

$^1$H NMR (DMSO) 1.8–2.2 (d OCOCH$_3$ 18H) 2.8–3.5 (m CONH CH$_2$ 8H) 3.6–4.2 (m CH—CH$_2$OCO 8H) 4.3–4.7 (m CO—CH$_2$—OAc 12H) 8.2–8.7 (m CONH, 4H exchangeable) 9.1–10.2 (m, NH—CO, 2H exchangeable)

5) Preparation of 4,4'-di-(hydroxy-acetylamino) 2,2', 6,6'tetra- (2-hydroxyethyl carbamoyl) 3,3', 5,5'-tetraiodo diphenyl 89 g (0.0544 mole) of the preceding product are stirred in the presence of 740 ml of N NaOH at room temperature for 2 h. The solution is then diluted to a volume of 3.8 l, then passed through H$^+$ and OH$^-$ ion exchange resins. The aqueous phases are then evaporated to dryness and the residue then crystallized from acetone. After washing with ether and drying in an oven at 50° C., compound No. 2 is obtained in a yield of 78.1%. TLC (CHCl$_3$ 55/MeOH 30/NH$_4$OH 10): R$_f$=0.45 Purity with respect to iodine: 98.30% H$_2$O content: 2.15%

$^1$H NMR (DMSO d$^6$) 2.6–6 (m 28H aliphatic 6 OH exchangeable) 8.2–8.6 (m CONH 4H exchangeable) 9.9–10.1 (m NHCO 2H exchangeable with D$_2$O)

EXAMPLE NO. 3

Preparation of 4,4'-bis-[(N-2,3-dihydroxy) propyl-acetylamino]-2,2', 6,6'-tetra-(2-hydroxyethyl carbamoyl) 3,3', 5,5'-tetraiodo-diphenyl (compound No. 3)

1) Preparation of 4,4'-diacetylamino-2,2', 6,6'-tetra-(2-acetoxyethyl carbamoyl) 3,3', 5,5'-tetraiodo diphenyl.

60 g of the product obtained in part 3 of the preceding example are suspended in 300 ml of acetic acid and 60 ml of acetic anhydride, then heated at 60° C. 2.5 ml of H$_2$SO$_4$ are added dropwise while the temperature is maintained at 70°—80° for ½ hour. The reaction mixture is then evaporated to dryness and the residue is taken up in ether, filtered off and dried. The desired product is obtained in a yield of 76%. The purity with respect to iodine is 102%. TLC (CH$_2$Cl$_2$ 90/MeOH 10): R$_f$=0.55

$^1$H NMR (DMSO) 2 (s. COCH$_3$ 18H) 3.3 and 3.9 (d CH$_2$—CH$_2$ 16H) 8.5 (n CONH 4H exchangeable) 10 (m, NH—CO, 2H exchangeable)

2) Preparation of 4,4'-diacetylamino 2,2', 6,6'-tetra-(2-hydroxy-ethyl carbamoyl)-3,3', 5,5'-tetraiodo diphenyl 99 g of the preceding product in 1.3 l of methanol containing 21.7 g of K$_2$CO$_3$ are added and the mixture is stirred for 3 h at room temperature. The precipitate formed is filtered off, washed with a minimal quantity of methanol and with ether. Yield: 100%

$^1$H NMR (DMSO d$^6$) 1.8 (s. COCH$_3$ 6H) 3.2 and 3.7 (2 m CH$_2$–CH$_2$, 20H) 8.5 (m, CONH, 4H exchangeable) 10 (m, NHCO, 2H exchangeable)

3) Preparation of 4,4'-bis [N-(2,3-dihydroxypropyl)-acetylamino]-2,2', 6,6'-tetra-(2-hydroxyethyl carbamoyl) 3,3', 5,5'tetraiododiphenyl (compound No. 3)

35 g of the preceding product are suspended in 200 ml of ethylene glycol. 0.186 mole of MeONA dissolved in methanol is added dropwise and the reaction mixture is heated for 1 h 30 min at 50° C. 18.2 ml of chloropropane diol are added at 10° C. The reaction mixture is heated at 50° C. for 44 h, while 0.062 mole of Na methylate in solution and 15 ml of chloropropane diol are added every 10 hours.

After evaporation of the methanol, the residual paste is taken up in acetone. After filtration of the salts, the ethylene glycol is evaporated under reduced pressure. The residue obtained solidifies in an acetone/isopropanol (70:30) mixture, then is filtered off and washed with ether.

The crude compound No. 3 obtained is then purified on a preparative HPLC column ($SiO_2$ $C_{18}$) in a yield of 70% TLC ($CH_2Cl_2$ 89/MeOH 20): $R_f$=0.15 TLC (Dioxan 90/$H_2O$ 10): $R_f$=0.7 Purity with respect to iodine: 98% HPLC purity: 97%

$^1$H NMR(DMSO)$_2$ (s, COCH$_3$ 6H) 3–3.6 (m partially exchangeable 26H aliphatic and 8 OH) 8.4 (s, CON$\underline{H}$, 4H exchangeable).

EXAMPLE 4

Preparation of 4,4'-bis-(2,3-dihydroxypropyl carbamoyl) 2,2', 6,6'-tetra-(2-hydroxy-propionylamino) 3,3', 5,5'-tetraiodo diphenyl (compound No. 4)

1) Preparation of 4-bromo 3,5-dinitro benzoic acid

A sulfuric-nitric acid mixture composed of 346 ml of $H_2SO_4$ and 346 ml of fuming $HNO_3$ is added dropwise to 100 g (0.49 mole) of p-bromobenzoic acid suspended in 900 ml of 98% $H_2SO_4$. The mixture is heated for 8 h at 80° C., then cooled and poured onto ice. The precipitate formed is filtered off, washed with 3×200 ml of $H_2O$, then suspended in 600 ml of $H_2O$. After the pH has been brought to 9–10 by means of 5N NaOH, the sodium salt is filtered off, then resuspended in 1 l of water and acidified to pH=1 by means of 5N HCl. The precipitate is then filtered off, washed with water and dried.

Yield 79% (95 g), M.p. 188° C. TLC (toluene 60/methyl ethyl ketone 35/formic acid 25): $R_f$=0.85 Purity with respect to bromine: 99%

$^1$H NMR (DMSO d$^6$) 8.5 ppm (s, 2H aromatic); 10.4 (s OH acid, exchangeable with $D_2O$)

2) Preparation of the methyl ester of 4-bromo 3-5-dinitro benzoic acid 115 g (0.398 mole) of 4-bromo 3,5-dinitro benzoic acid are dissolved in 840 ml of methanol. After addition of 57.5 ml of 98% $H_2SO_4$, the mixture is heated at reflux for 3 hours. After cooling, the product precipitates. The reaction product is filtered off, washed with $H_2O$ (3×300 ml), then by 100 ml of methanol.

Yield: 90%

M.p.: 122°–124° C. (124° C. in the literature) TLC (toluene/methyl ethyl ketone/formic acid: 60/35/25): $R_f$=0.95

$^1$H NMR (DMSO d$^6$) 4.1 (s, COOCH$_3$, 3H) 8.75 (s 2H arom.)

3) Preparation of 4,4'-dimethoxycarbonyl 2,2', 6,6'-tetranitro diphenyl

To a solution of 60 g (0.196 mole) of the preceding product in 260 ml of paraxylene preheated to 80° C. are added 12.6 g of copper. The mixture is then heated at 160° C. for 1 h 30 with vigorous stirring. 6.4 g of copper are added and the mixture is maintained at 160° C. for a further hour. The mixture is cooled, then filtered through Celite. After evaporation, the residue is taken up in ethyl acetate.

Yield: 73%

M.p.: 171° C. TLC (toluene/methyl ethyl ketone/formic acid: 60/35/25): $R_f$=0.9

$^1$H NMR (DMSO d$^6$) 4.1 (s COOCH$_3$, 6H) 9 (s 4H arom.)

4) Preparation of 4,4'-bis-(2,3-dihydroxypropyl carbamoyl)2,2', 6,6'-tetranitro diphenyl 21 g (0.046 mole) of the preceding product are dissolved in 240 ml of DMAC. After the reaction mixture has been heated at 60° C., 17.5 g of aminopropane diol in 50 ml of DMAC are added dropwise. After being stirred for 1 h 30 min., the reaction mixture is cooled, then poured into 1.5 l of water. The precipitate is then filtered off, washed with $H_2O$ and then with ether.

M.p. : 130° C. TLC (toluene/methyl ethyl ketone/formic acid: 60/35/25): $R_f$=0.15

$^1$H NMR (DMSO) 3.4–3.9 (m CH—CH$_2$ 12H) 4.5–5 (m OH exchangeable 4H) 9.1 (s 4H arom)

5) Preparation of 4,4'-bis (2,3-dihydroxypropyl carbamoyl) 2,2'-6,6'-tetraamino diphenyl A suspension of 9 g of the preceding product is added to a $H_2O$/MeOH mixture (150 ml/150 ml) containing 30 g of Raney nickel and the mixture is stirred under $H_2$ pressure (3.10$^5$ Pa) for 24 h at room temperature. After the reaction mixture has been filtered through Celite, the filtrate is evaporated and the residue is crystallized from absolute methanol.

Yield: 50%, M.p.=250° C. TLC (dichloromethane/methanol: 80/20): $R_f$=0.05

6) Preparation of 4,4'-bis-(2,3-dihydroxypropyl carbamoyl) 2,2', 6,6'-tetraamino 3,3', 5,5'-tetraiodo diphenyl A solution of 20.4 g of $I_2$ (0.084 mole) and 13.3 g (0.0804 mole) of KI in 20 ml of $H_2O$, prepared immediately before use, is added dropwise to a solution of 6 g of the preceding product in 600 ml of $H_2O$ and 60 ml of 33% ethylamine. At the end of the addition, the mixture is heated for 3 h at 80° C. After addition of 10 ml of a solution of 6.8 g of 12 (0.0268 mole) and 4.4 g (0.0268 mole) of KI in water, the mixture is heated for 3 h at 80° C., then left to stand overnight at room temperature. The precipitate is filtered off, washed with water, bisulfite and acetone, and dried.

Yield=50% TLC (dichloromethane/methanol: 80/20): $R_f$=0.3 Purity with respect to iodine: 97%

$^1$H NMR (DMSO d$^6$) 3.1 (m complex) 4.4 and 8 (multiplets exchangeable with $D_2O$)

7) Preparation of 4,4'-bis-[2,3-di-(2-acetoxy propionyloxy)-propyl-carbamoyl]2,2', 6,6'-tetra-(2-acetoxy-propionyl amino) 3,3', 5,5'-tetraiodo diphenyl.

5 g (0.033 mole) of acetylated lactic acid chloride and 4.7 ml (0.033 mole) of triethylamine are added simultaneously to a solution cooled to 5° C. of 2.7 g (0.0024 mole) of the preceding product in 15 ml of DMAC. During the addition, the temperature is maintained below 10° C., then the mixture is heated slowly to 40° C. during 8 h.

1.08 g (0.0072 mole) of acetylated lactic acid chloride and 1.01 ml (0.0072 mole) of triethylamine are then added simultaneously at 10° C. The reaction mixture is then heated at 40° C. for 12 h. After removal of the triethylamine hydrochloride formed by filtration and evaporation of the DMAC, the residue is poured into water. The crystals obtained are washed with water, then with ether.

Yield: 80% Purity with respect to iodine: 105% TLC (toluene 60/methyl ethyl ketone 35/formic acid 25): $R_f$=0.6 (3 spots joined together)

$^1$H NMR (DMSO d$^6$) 1.3 (multiplet C—CH$_3$, 24H) 2.1 (s. COCH$_3$ 24H) 3.1–5.4 (multiplet, partially exchangeable $\underline{N}$H—CO4H; C—C$\underline{H}$—C 12H, CO—C$\underline{H}$—C 8H)

8) Preparation of 4,4'-bis-(2,3-dihydroxypropyl carbamoyl) 2,2', 6,6'-tetra (2-hydroxypropionylamino)-3,3', 5,5'-tetraiodo diphenyl (compound No. 4)

31.5 g (0.0168 mole) of the preceding product are added to a suspension of 27.6 g of $K_2CO_3$ in 400 ml of methanol and the mixture is stirred for 4 h at room temperature. The solution is then evaporated and passed through a $H^+$ ion exchange resin. The product obtained after evaporation is washed with acetone.

Yield: 50% Purity with respect to iodine: 96.6% Water content: 1.83%

M.p.=220° TLC (dichloromethane/methanol: 80/20): $R_f$=0.7 TLC (butanol/water/acetic acid: 50/25/11): $R_f$=0.35

$^1$H NMR (DMSO) 1.2 (s. C—C$\underline{H}_3$, 12H) 3 to 6 (3 complex multiplets

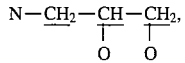

10H, CO—C$\underline{H}$—O 4H, 8 OH, exchangeable) 9–9.5 (1 multiplet exchangeable with $D_2O$, —N$\underline{H}$—CO, CO—N$\underline{H}$—, 5H).

EXAMPLE 5

Preparation of 2,2', 4,4', 6,6'-hexa-(2-hydroxy-propionyl amino) 3,3'-5,5'-tetraiodo diphenyl (compound No. 5)

1) Preparation of 4,4'-dicarboxy 2,2', 6,6'-tetranitro diphenyl 55.4 g (0.123 mole) of the product obtained in part 3 of the preceding example is suspended in 600 ml of $H_2O$ containing 10.6 g (0.27 mole) of NaOH. The mixture is heated at 80° C. for 6 h, then cooled. The aqueous phase is washed with 2×200 ml of dichloromethane, then acidified by means of HCl. The precipitate is washed with $H_2O$ (3×300 ml), then dried.

Yield: 100%. M.p.>300° C. TLC (toluene/methyl ethyl ketone/formic acid: 60/35/25): $R_f$=0.75

$^1$H NMR (DMSO) 8.9 (s. 4H arom) 14 (2 2H COO$\underline{H}$ exchangeable with $D_2O$).

2) Preparation of 4,4'-diamino 2,2', 6,6'-tetranitro diphenyl 51 g (0.120 mole) of the preceding product is dissolved in 320 ml of 30% oleum, then diluted with 280 ml of 1,2-dichloroethane. The mixture is heated to 45° C. Then, 23 g of $NaN_3$ are added in portions, while the temperature is maintained below 50° C. After the end of the addition, the reaction mixture is heated progressively to 90° C., then stirred for 3 hours. 9 g of $NaN_3$ are then added at a temperature lower than 50° C. The mixture is heated at 90° C. for 2 h. After cooling to room temperature and decantation, the lower phase is poured slowly into an ice-water mixture. The product precipitates and the suspension is stirred for ½ hour at 60° C., then left overnight at room temperature. After filtration, washing with water, then with ether, the desired product is obtained in a yield of 90%.

M.p.>300° C. TLC (toluene 60/methyl ethyl ketone 35/formic acid 25): $R_f$=0.9

$^1$H NMR (DMSO) 5.8 (1s $NH_2$ 4H disappears with $D_2O$) 7.5 (s, 4H arom)

3) Preparation of 4,4'-di-(2-acetoxypropionylamino) 2,2', 6,6'-tetranitro diphenyl 59.5 g (0.163 moles) of the preceding product are added in portions to a solution of 54.3 g (0.358 moles) of acetylated lactic acid chloride in 300 ml of anhydrous DMAC. The temperature is maintained below 10° C. during the addition, then is allowed to rise to room temperature and the mixture is stirred for 2 h. After evaporation of the DMAC, the residue is poured into an ice/water mixture to give the desired product in the form of crystals. After washing with water and then with methanol, the yield is 83%.

M.p.=264° C. TLC (toluene/methyl ethyl ketone/formic acid: 60/35/25): $R_f$=0.7

$^1$H NMR (DMSO d$^6$) 1.5 (d C—C$\underline{H}_3$ 6H) 2.1 (s, CO C$\underline{H}_3$ 6H) 5.1 (d CO—C$\underline{H}$—C 2H) 8.7 (s 4H arom) 14 (s CO—N$\underline{H}$-phenyl 2H exchangeable)

4) Preparation of 4,4'-di-(2-hydroxypropionyl amino) 2,2'-6,6'-tetraamino diphenyl 10 g (0.0167 mole) of the preceding product are added to a mixture of MeOH (460 ml) and water (160 ml) containing 40 g of Raney nickel and the mixture is stirred under $H_2$ pressure (3.10$^5$ Pa) for 24 h at room temperature. After removal of the catalyst by filtration and evaporation of the filtrate, the residue is crystallized from ethanol. The final product is obtained after filtration in a yield of 60%. TLC (dichloromethane/methanol: 80/20): Rf 0.45

$^1$H NMR (DMSO d$^6$) 1.3–1.5(C—C$\underline{H}_3$ 6H) 4.1 (s N$\underline{H}_2$ 8H exchangeable) 5 (m C—C$\underline{H}$—CO, 2H) 5.5 (s. C—OH 2H, exchangeable) 6.4 (s 4H arom) 8.8 (s CO—N$\underline{H}$-phenyl 2H)

5) Preparation of 4,4'-di-(2-hydroxypropionyl amino) 2,2', 6,6'-tetraamino 3,3', 5,5'-tetraiodo diphenyl To a solution of 6 g (0.129 mole) of the preceding product in a mixture of water (800 ml) and 33% ethylamine (80 ml) is added dropwise a solution of 100 ml of $H_2O$ containing 41.7 g of $I_2$ and 31 g of KI. As soon as the addition is complete, the mixture is heated for 6 h at 80° C., then stirred overnight at room temperature. The precipitate which forms is filtered off, washed with $H_2O$, then with a solution of bisulfite and, finally, dried. The final product is obtained in a yield of 80%. Purity with respect to iodine: 97% TLC (toluene/methyl ethyl ketone/formic acid: 60/35/25): $R_f$=0.2

$^1$H NMR (DMSO) 1.3–1.5

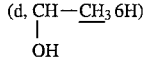

3.7–4.4

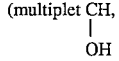

4H, $HN_2$ 8H, partially exchangeable with $D_2O$) 9.1 (s, CO-N $\underline{H}$-phenyl, 2H exchangeable)

6) Preparation of 4,4-di[(2-acetoxy 2-propionyloxy)-propionyl amino]2,2', 6,6'-tetra-(2-acetoxypropionyl amino) 3,3', 5,5'-tetraiodo diphenyl To a solution of 9.5 g (0.01065 mole) of the preceding product and 20 ml of triethylamine in 100 ml of anhydrous DMAC are added dropwise 21.3 g of acetylated lactic acid chloride. The reaction mixture is heated for 10 h at 50° C., then it is left to stand for 12 h at room temperature; the DMAC is evaporated in a vacuum and the residue is poured into water. The precipitate obtained is taken up in CHCl$_3$. The chloroform phase is washed with water, dried over MgSO$_4$ and evaporated. The residue obtained crystallizes from isopropyl ether and gives the final product in a yield of 73%. Purity with respect to iodine: 105% TLC (toluene/methyl ethyl ketone/formic acid: 60/35/25): $R_f$=0.6 (3 spots joined together)

$^1$H NMR (DMSO) 0.8 to 1.6 (multiplet CH—C$\underline{H}_3$ 24H) 2 (s OCOC$\underline{H}_3$ 18H) 4.4 to 5.4 (m —C$\underline{H}$8H) 7.8 to 12 (multiplet - N$\underline{H}$- 6H exchangeable)

7) Preparation of 2,2', 4,4', 6,6'-hexa-(2-hydroxy propionyl amino) 3,3', 5,5'-tetraiodo diphenyl (compound No. 5)

3 g of $K_2CO_3$ are added to a solution of 6 g (0.0038 mole) of the preceding product in 120 ml of MeOH. After being stirred overnight at room temperature, the solution is evaporated to dryness, then diluted with $H_2O$. This solution is passed through a $H^+$ ion exchange resin, then evaporated. The residue is crystallized from acetone and the crystals are washed with petroleum ether.

Yield: 35% Purity with respect to iodine: 93% TLC (dichloromethane/methanol: 60/40): $R_f$=0.9 TLC (butanol/water/acetic acid: 50/25/11): $R_f$=0.5=0.6

$^1$H NMR (DMSO) 0.6–1.6 (multiplet CH—$CH_3$ 18H) 3.6–4.8 (multiplet -C$\underline{H}$—OH 12H, partially exchangeable) 8.5–9.8 (multiplet-N$\underline{H}$, 6H exchangeable)

EXAMPLE 6

Preparation of 2,2'-di-(2-hydroxypropionyl amino) 4,4', 6,6'-tetra (2-hydroxyethyl carbamoyl) 3,3', 5,5'-tetraiodo diphenyl (compound No. 6)

1) Preparation of 4-bromo isophthalic acid 10 g (54 mmoles) of 5-bromo xylene are dissolved in 200 ml of water containing 49 g (0.22 mole) of potassium permanganate. The reaction mixture is refluxed for 48 hours.

The manganese dioxide formed is filtered onto Celite and the filtrate is acidified by a 2N solution of HCl. The white precipitate obtained is filtered off, washed with water and dried in an oven.

Yield: 43% TLC (isopropanol/ethyl acetate/ammonia: 25/35/40) $R_f$=0.67

M.p.>260° C. Purity with respect to bromine: 106%

IR (KBr): 3000 cm$^{-1}$ (vOH), 1680 (vCO)

$^1$H NMR (DMSO): disappearance of the methyl protons

2) Preparation of 4-bromo 5-nitro isophthalic acid 235 ml of a sulfuric-nitric acid mixture ($HNO_3$:3.5 ml+$H_2SO_4$: 20 ml) are added dropwise at 0° C. to a solution of 4-bromo isophthalic acid (10 g) in 100 ml of sulfuric acid. The reaction mixture is heated at 50° C. overnight until the starting compound has disappeared. The reaction product obtained is then precipitated on crushed ice. After filtration, washing with water and drying, 10.8 g of product are recovered in a yield of 91%. TLC (toluene/methyl ethyl ketone/formic acid 60/25/25): $R_f$:0.68 TLC (isopropanol/ethyl acetate/ammonia 25/35/40): $R_f$:0.4

M.p.>260° C. Purity with respect to bromine: 99.3%

IR (KBr): 3000 cm$^{-1}$ (vOH); 1700 (vCO), 1590 (vC=C arom.); 1540 (vNO$_2$)

$^1$H NMR (DMSO): δ8.4–8.5 ppm (2 split doublets, 2H aromatic)

3 Preparation of dimethyl 4-bromo 5-nitro isophthalate 16 ml of concentrated sulfuric acid are added to a solution of 105 g (0.23 mole) of 4-bromo 5-nitro isophthalic acid in 60 ml of methanol. The reaction mixture is refluxed for 15 hours. After being left overnight at room temperature, the crystallized product is filtered off, washed with water, then dried in an oven.

Yield: 91% TLC (toluene/methyl ethyl ketone/formic acid 60/25/25): $R_f$=0.82 TLC (dichloromethane): $R_f$:0.7

M.p.=90° C. Purity with respect to bromine: 100%

IR (KBr): 1735 cm$^{-1}$ (vCO), 1600 (vC=C); 1540 (vNO$_2$)

$^1$H NMR (CDCl$_3$): δ4 ppm (singlet, 6H, 2CH$_3$ of the esters) 8 ppm (2 multiplets, 2H aromatic)

4) Preparation of 2,2'-dinitro 4,4', 6,6'-tetra-methoxycarbonyl diphenyl 40.5 g of copper are added to a solution of dimethyl 4-bromo 5-nitro isophthalate (71 g, 0.22 mole) in 240 ml of p-xylene. The mixture is heated at reflux for 24 hours. After being allowed to cool to room temperature, the reaction mixture is filtered and the filtrate is evaporated under reduced pressure. The residue obtained is crystallized from isopropyl ether. 42.5 g of product are obtained.

Yield: 80% TLC (hexane/ethyl acetate v/v) $R_f$:0.6 TLC (CH$_2$Cl$_2$) $R_f$:0.4

M.p. : 116°–119° C.

IR (KBr): 1720 (vCO), 1530 (vNO$_2$)

$^1$H NMR (CDCl$_3$): δ8.8 ppm (multiplet, 4H aromatic), δ4 ppm (singlet, 6H, 2 methyl at 4,4'); δ3.6 ppm (singlet, 6H, 2 methyl at 6,6').

5) Preparation of 2,2'-dinitro 4,4', 6,6'-tetra-(2-hydroxyethyl carbamoyl) diphenyl 58.8 g of ethanolamine are added to a suspension of the preceding product (48.3 g; 0.1 mole) in 360 ml of methanol. After being refluxed for 48 hours, the reaction mixture is left to stand at room temperature for 24 hours. The precipitate formed is filtered off, then taken up in acetone. After drying, 50.5 g of the product are obtained in a yield of 84%. TLC (dioxane/water: 9/1): $R_f$ 0.75 TLC (dichloromethane/methanol: 8/2): $R_f$ 0.23

IR (KBr): 3430 cm$^{-1}$ (vN—H), 3200–3500 (vOH), 3090 (vH aromatic) 2900 (vH aliphatic), 1640 (vCO—NH), 1000 (vC=C arom.), 1545 (vNO$_2$)

$^1$H NMR (DMSO, H$_2$O): δ8.4 and 8.9 ppm (2 doublets, 4H aromatic) δ3.25 and 3.6 ppm (2 multiplets, 16H CH$_2$ aliphatic )

6) Preparation of 2,2'-diamino 4,4', 6,6'-tetra-(2-hydroxyethyl carbamoyl) diphenyl A methanolic solution (250 ml) of 15 g of the preceding product is stirred under an atmosphere of hydrogen (pressure of 3.10$^5$ Pa) for 1 h30 in the presence of 10% palladised charcoal (2.5 g). The catalyst is then removed by filtration. After evaporation of the solvent under reduced pressure, the residue is recrystallized from ether and 12.9 g of product are obtained in a yield of 90.6%. TLC (dichloromethane/methanol: v/v): $R_f$ 0.45

$^1$H NMR (DMSO): δ8.1 and 8.35 ppm (2 multiplets, 2H exchangeable with D$_2$O, NH); δ7.05 ppm (multiplet 4H, aromatic), δ4.4 ppm (multiplet, 8H exchangeable with D$_2$O, NH$_2$, OH); δ3.05 and ppm (2 multiplets, 16H, CH$_2$ aliphatic).

7) preparation of 2,2'-diamino 4,4', 6,6'-tetra-(2-hydroxyethyl carbamoyl) 3,3', 5,5'-tetraiodo diphenyl 35 ml of iodine chloride (70% in iodine) are added dropwise with vigorous stirring and at room temperature to a solution of the preceding product (23.6 g) in 470 ml of water. The reaction medium is heated at 40° C. for 2 hours. After being left to stand for half an hour at room temperature, the excess iodine is destroyed by sodium hydrosulfite and the precipitate is filtered off, washed with water and then with ethanol. It is dried in an oven at 60° C. to give 40.2 g of product in a yield of 87.5% TLC (methylene chloride/methanol v/v): $R_f$ 0.87 TLC (butanol/water/acetic acid 50/25/11): $R_f$ 0.45 Purity with respect to iodine: 103%

$^1$H NMR (DMSO): δ7.8–8.5 ppm (2 m, 4H, NH), δ4.15 ppm (singlet, 4 exchangeable, OH); δ2.6–3.8 ppm (2 multiplets, 16H, CH$_2$ aliphatic) HPLC Lichrospher 100 rp 8.5µ; 12.5 cm MeOH 65/water 35: 1 ml/min., purity 99%

8) Preparation of 2,2'-di-(2-acetoxypropionyl amino) 4,4', 6,6'-tetra-(2-acetoxyethyl carbamoyl) 3,3', 5,5'-tetraiodo diphenyl 5.3 g of O-acetylated lactic acid (34.7 moles) are added dropwise at 0° C. to a solution containing 3 g of the preceding product in 35 ml of anhydrous DMAC. The suspension is then heated at 60° C. for 21 hours. The DMAC is evaporated under reduced pressure. The oil obtained is retreated with dichloromethane, washed with water then dried over sodium sulfate. After evaporation in a vacuum, the residue is precipitated with a mixture of methylene chloride and isopropyl ether, then filtered off to give 3.6 g of product in a yield of 78.3%. TLC (methylene chloride/methanol 8/2): $R_f$ 0.88 TLC (butanol/water/acetic acid 50/25/11): $R_f$:0.82 TLC (isopropanol/ethyl acetate/ammonia: 25/35/40): $R_f$:0.86 Purity with respect to iodine: 98.2%

IR (KBr): 3340 (vN—H), 1730 cm$^{-1}$ (vCO ester); 1650 (vCO—NH)

$^1$H NMR (CDCl$_3$): δ5 ppm (multiplet, 1H, C$\underline{H}$ lactic); 4.3 ppm (m, 2H, C$\underline{H}_2$—CO); 3.7 ppm (multiplet, 2H, N—C$\underline{H}_2$); 2.1 ppm (singlet, 18H, O—CO—C$\underline{H}_3$); 1.5 ppm (d, 18H, C$\underline{H}_3$ lactic).

9) Preparation of 2,6-di-(2-hydroxypropionyl amino)-2,4,4', 6,'-tetra-(2-hydroxyethyl carbamoyl) 3,3', 5,5'-tetraiodo diphenyl (compound No. 6)

The O-acylated compound obtained in the preceding step (49 g) dissolved in 600 ml of ethanol is treated with an ethanolic solution (200 ml) of sodium hydroxide (16 g). The reaction mixture is stirred for 3 hours. The residue after evaporation of the solvent is washed with acetone, then precipitated with ether. The product is filtered off and desalted by being passed through H$^+$(IRN77) and OH$^-$(IRN 78) resins. The water is evaporated under reduced pressure and the residue is precipitated with acetone, then washed with ether to give 23 g of crude product.

EXAMPLE 7

Preparation of 2,2'-di-(2-hydroxy-acetylamino)-4,4', 6,6'-tetrakis-(2,3-dihydroxypropyl carbamoyl) 3,3', 5,5'-tetraiodo diphenyl (compound No. 7).

1) Preparation of 2,2'-dinitro 4,4', 6,6'-tetrakis-(2,3-dihydroxypropyl carbamoyl) diphenyl 74 g of aminopropane diol are added dropwise to a preheated solution of a product (38.7 g; 81.3 moles) in part 4 of the preceding example in 255 ml of methanol. The mixture is heated at reflux for 12 h. After being allowed to cool to room temperature, the reaction mixture is filtered and the filtrate is evaporated under reduced pressure. The residue is dissolved in 750 ml of water, then purified by passage through a column of a H$^+$resin (IRN 77). The water is eliminated by distillation and the residue is taken up in isopropyl ether. The product obtained is filtered off and dried to give 55.3 g in a yield of 95.5%. TLC (dioxan/water: 9/1) $R_f$:0.65

$^1$H NMR (DMSO): δ3.6 and 3.3 ppm (2 m, 20H, C$\underline{H}_2$ and C$\underline{H}$ aliphatics) δ4.55 ppm (1 m, 8H exchangeable with D$_2$O, OH) δ8.95 and 8.5 ppm (2 m, 4H aromatic)

IR (KBr) 3300 cm$^{-1}$ (vOH) 1630 (vCO—NH); 1520 and 1310 (vNO$_2$)

2) Preparation of 2,2'-diamino 4,4', 6,6'-tetrakis-(2,3-dihydroxy-propyl carbamoyl) diphenyl An aqueous solution (600 ml) of the preceding compound (28.9 g; 40.6 mmole) is stirred under an atmosphere of hydrogen (pressure of 4.10$^5$ Pa) for 5 hours in the presence of 10% palladised charcoal (6 g). The catalyst is then removed by filtration. After evaporation of the solvent under reduced pressure, the residue is taken up in methanol, concentrated then neutralized with isopropyl ether.

24.7 g of product are obtained in a yield of 93.3% TLC (dioxan/water: 9/1): $R_f$ 0.6

$^1$H NMR (DMSO) δ3.3 and 3.1 ppm (1 multiplet, 20 $\underline{H}$, C$\underline{H}_2$ and C$\underline{H}$ aliphatic) δ4.45 ppm (1 multiplet, 12$\underline{H}$ exchangeable with D$_2$O, 8 OH+2 N$\underline{H}_2$); δ7.1 ppm (1 multiplet, 4H aromatic); δ8.4 and 8.1 ppm (2 multiplets, 4H exchangeable with D$_2$O, 4 NH)

IR (KBr) 3100–3500 cm$^{-1}$ (vOH, NH$_2$) 1620(vCONH)

3) Preparation of 2,2'-diamino 4,4', 6,6'-tetrakis-(2,3-dihydroxypropyl carbamoyl) 3,3', 5,5'-tetraiodo diphenyl 126 ml of iodine chloride (70% in iodine) are added dropwise with vigorous stirring and at room temperature to a solution of the compound obtained in the previous step (63.9 g; 98 moles) in 300 ml of water. The reaction mixture is maintained at 45° C. for 7 hours and then for 16 hours at room temperature. After evaporation, the residue is taken up in absolute ethanol. The solid collected by filtration is then purified after being dissolved in 1 l of water by successive passages through H$^+$(IRN 77) and OH$^-$(IRN 78) resins. The resulting solution is evaporated to dryness. After washing with ether and drying, 73.7 g of product are isolated in a yield of 65%. TLC (dioxan/water: 9/1) $R_f$:0.86 Purity with respect to iodine: 98.1%

$^1$H NMR (DMSO) δ3.95 ppm (1 multiplet, 20H C$\underline{H}_2$ and C$\underline{H}$ aliphatic); 4.6 ppm (1 multiplet, 12$\underline{H}$ exchangeable with D$_2$O, 8 O$\underline{H}$ and 2 N$\underline{H}_2$); 8.2 ppm (1 multiplet, 4$\underline{H}$ exchangeable, NH)

4) Preparation of 2,2'-di-(2-acetoxyacetylamino) 4,4', 6,6'-tetrakis-/2,2-di(2-acetoxy-acetoxy)propyl carbamoyl/3,3', 5,5'-tetraiodo diphenyl 100.4 g of O-acetylated glycolic acid chloride (0.735 mole) are added dropwise to a solution of 42.5 g (36.7 moles) of the preceding compound in 300 ml of anhydrous DMAC. The reaction mixture is stirred at room temperature for 22 hours until the starting amine has disappeared (checked by the thiocol test). The DMAC is evaporated under reduced pressure, the residue obtained is extracted with dichloromethane, washed with water then dried over Na$_2$SO$_4$. After being concentrated and taken up in ethyl ether 72.1 g of product are obtained in a yield of 91%. TLC (dioxan/water: 9/1): $R_f$ 0.9. Purity with respect to iodine: 99.2%

5) Preparation of 2,2'-di-(2-hydroxy acetylamino) 4,4', 6,6'-tetrakis-(2,2-dihydroxypropyl carbamoyl) 3,3', 5,5'-tetraiodo diphenyl (compound No. 7)

69 g (0.032 mole) of the product described in the preceding step are deprotected by dissolution in 100 ml of absolute ethanol to which 1.3 l of a 0.5N solution of ethanolic sodium hydroxide is added. The reaction mixture is stirred for ¾ hour. The precipitate formed is filtered off, dried and then desalted by passages through H$^+$(IRN 77) and OH$^-$(IRN 78) resins. The water is removed by distillation and the residue is taken up in ethyl ether. 28.7 g of product are recovered and purified by HPLC (RP 18). Overall yield: 56.4% TLC (dioxan/water: 9/1): $R_f$:0.55 HPLC purity: 98.3%

$^1$H NMR (DMSO) δ8.95 ppm (multiplet, 2H exchangeable with D$_2$O, —N$\underline{H}$—CO); δ8.35 ppm (multiplet, 4H exchangeable with D$_2$O, —CO—N$\underline{H}$); δ5.2 ppm (multiplet, 2H exchangeable with D$_2$O, —NHCOC$\underline{H}_2$O$\underline{H}$); δ4.7 ppm (multiplet, 8H exchangeable with D$_2$O, —CONHC$\underline{H}_2$—C$\underline{H}$OH—C$\underline{H}_2$O$\underline{H}$); δ63.4 ppm (multiplet, 24H exchangeable with aliphatic protons)

EXAMPLE 8

Preparation of 3,3'-bis-/(3-hydroxy 2-hydroxy-methyl)propionyl/ amino 5,5'-bis/N-methyl-N-(2,3-dihydroxy-propyl)/carbamoyl 2,2', 4,4', 6,6'-hexaiodo diphenyl (compound No. 8).

1) Preparation of 3-iodo 5-nitro benzoic acid

To 122 g (0.53 mole) of H$_5$IO$_6$ and 400 g (1.57 mole of iodine dissolved in 2750 ml of 20% oleum at 10° C. by stirring for 30 minutes are added 120 g (0.72 mole) of 3-nitro benzoic acid. After being stirred at room temperature for 12 hours, this solution is poured slowly onto ice. The precipitate formed is filtered off, then washed with a 20% solution of sodium bisulfite before being dissolved in a solution of sodium hydroxide, followed by filtration through paper. After acidification with HCl, 170 g of white crystals are obtained which are filtered off and dried.

Yield=81%

M.p.=172° C. TLC (toluene 60/methyl ethyl ketone 25/HCOOH 5) $R_f$=0.75 Purity with respect to iodine=99%

$^1$H NMR (DMSO) δ8.5 ppm (s, 2H aromatic); δ8.7 ppm (s, 1H aromatic); 13 ppm (m, COO$\underline{H}$ 1H exchangeable with $D_2O$)

2) Preparation of the methyl ester of 3-iodo 5-nitro benzoic acid 180 g (0.614 mole) of the compound obtained in 1 dissolved in 1800 ml of methanol and 10 ml of 98% $H_2SO_4$ are heated at reflux for 24 hours. After evaporation of two-thirds of the methanol, the solution obtained is cooled and the ester which precipitates is filtered off. After dissolution of the product in 2000 ml of ether, the ethereal phase is washed with 1000 ml of water, then dried over $MgSO_4$ and evaporated to dryness. 181 g of white crystals are obtained.

Yield: 90%

M.p.=88° C. Purity with respect to iodine 99% TLC ($CH_2Cl_2$ 70-MeOH 30): $R_f$=0.95

IR 1720 ($COOCH_3$); 1520 ($NO_2$).

$^1$H NMR (DMSO) δ3.9 ppm (s, COOC$\underline{H}_3$, 3H); δ8.5 ppm (s, 2H aromatics); δ8.7 ppm (s, 1H aromatic).

3) Preparation of 5,5'-dimethoxycarbonyl 3,3'-dinitro diphenyl 86 g (0.28 mole) of the compound obtained in step 2) are heated to 220° C. After addition of 86 g of copper, the temperature is raised gradually to 270° C. and a further 20 g of copper are added. The mixture is maintained at this temperature for 1 hour before being cooled. After extraction with $CH_2Cl_2$ and filtration through Celite, the organic phase is evaporated to dryness.

The residual paste is washed with 2×500 ml of petroleum ether, then taken up in ether. The brown precipitate formed is filtered off, then purified by means of chromatography on silica. After evaporation, 20 g of brown crystals are obtained.

Yield=40%

M.p.=159° TLC ($CH_2Cl_2$): $R_f$=0.6

$^1$H NMR (DMSO): δ3.9 ppm (s, COOC$\underline{H}_3$, 6H); δ8.5 ppm (2s, 4H aromatic); δ8.7 ppm (1s, 2H aromatic)

4) Preparation of 5,5'-dicarboxy 3,3'-dinitro diphenyl 14 g (0.038 mole) of the compound obtained in 3) are heated at reflux for 18 h in 100 ml of a 25% aqueous solution of NaOH.

The solution obtained is cooled; after acidification, the precipitate formed is extracted with ethyl acetate and washed with water. After evaporation and washing with ether, 12 g of white crystals are obtained.

Yield =95%

M.p.>300° C. TLC (toluene 60/methyl ethyl ketone 25/HCOOH 25): $R_f$=0.8

$^1$H NMR (DMSO): δ5.3 ppm (m, COO$\underline{H}$, 2H exchangeable with $D_2O$); δ8.65 to 8.8 ppm (3s, 6H aromatic).

5) Preparation of 3,3'-dinitro 5,5'-bis-(N-methyl N-2,3-dihydroxy propyl) carbamoyl diphenyl 1.66 g (0.005 mole) of the compound obtained in 4) are added to a solution of 60 ml of $SOCl_2$ and 0.1 ml of dimethylformamide. The solution is heated at reflux for 5 hours. After distillation of the $SOCl_2$, the paste obtained is dissolved in $CH_2Cl_2$ and poured dropwise at 5° C. into a solution containing 2.1 g (0.02 mole) of N-methyl amino 2,3-propanediol and 2.8 ml (0.02 mole) of triethylamine dissolved in 20 ml of dimethylacetamide. After addition, the mixture is stirred at room temperature for 12 h. After filtration of the triethylamine hydrochloride, the solvent is evaporated. The paste obtained is purified by passage through a H$^+$/OH$^-$resin, then by chromatography on silica. After evaporation of the solvents 1.9 g of white crystals are obtained.

Yield=70% TLC ($CH_2Cl_2$ 85/MeOH 15) $R_f$=0.35

IR: 3300–3500 (OH); 1600

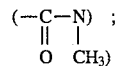

1520 ($NO_2$)

$^1$H NMR (DMSO): δ3 ppm

δ3.2 ppm to 4 ppm (m, $\underline{CH_2}$—$\underline{CH}$—$\underline{CH_2}$, 10H) ; δ4.4 ppm to 5.5 ppm

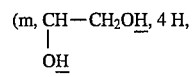

exchangeable with $D_2O$); δ8.3 ppm (s, 4H arom); 8.7 ppm (s, 2H arom)

b 6) Preparation of 3,3'-diamino 5,5'-bis-[N-methyl N-(2,3-dihydroxypropyl) carbamoyl]2,2', 4,4', 6,6'-hexaiodo diphenyl a) Reduction of the nitro groups:

1.6 g (0.0031 mole) of the compound obtained in 5) dissolved in 200 ml of methanol in the presence of 1 g of 10% Pd/C are shaken in a 500 ml autoclave for 2 h30 at 40° C. under a hydrogen pressure of 6.10$^5$ Pa. After removal of the catalyst by filtration and evaporation of the solvent, a paste is obtained. TLC ($CH_2Cl_2$ 80/MeOH 20): $R_f$=0.1 b) Iodination by ICl

To the paste obtained in a) dissolved in 100 ml of a mixture MeOH/$H_2O$:50/50 are added dropwise 2.1 ml (0.027 mole) of a 70% solution of ICl. When the addition is complete, the reaction mixture is heated at 60° C. for 4 h, then left to stand at room temperature for 12 h. The brown solution obtained is poured with stirring into 200 ml of water. The precipitate formed is filtered off, then washed with a 20% solution of sodium bisulfite and $H_2O$. The product is taken up in ether, then dried. 3 g of white crystals are obtained.

Yield=80% Purity with respect to iodine=99% TLC ($CH_2Cl_2$) 85/MeOH 15): $R_f$=0.4

$^1$H NMR (DMSO) δ2.9 and 3.1 ppm (s, N—C$\underline{H}_3$ Z) (s, N—C$\underline{H}_3$ E) 6H; δ3.2 to 4 ppm (m, $CH_2$—CH—$CH_2$, 10H); δ4.4 to 4.8 ppm

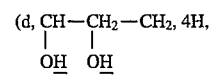

exchangeable with $D_2O$) δ5.5 ppm (s, $NH_3$, 4H exchangeable with $D_2O$)

7) Preparation of 3,3'-diamino 5,5'-bis/N-methyl N-(2,3-diacetoxypropyl) carbamoyl/ 2,2, 4,4', 6,6'-hexaiodo diphenyl To 1.2 g (0.001 mole) of the compound obtained in 6) dissolved in 12 ml of pyridine 1.5 ml of acetic anhydride are added dropwise at 5° C. After the reaction mixture has been stirred at room temperature for 18 h, the crude product is poured into ice-cold water, acidified with 30 ml of 5N HCl. The precipitate formed is filtered off, then taken up in $CH_2Cl_2$. The organic phase is washed with water, then dried over $MgSO_4$. After evaporation, 1 g of white crystals are obtained which are washed with ether and dried.

Yield: 73% Purity with respect to iodine: 98% TLC ($CH_2Cl_2$ 85/MeOH 15): $R_f$=0.8

IR 3300–3450:—$NH_2$; 1720:

$$O-\underset{\underset{O}{\|}}{C}-CH_3;\ 1620:\ \underset{\underset{O}{\|}\ \ \underset{CH_3}{|}}{C-N}\ ;$$

1580: $NH_2$ $^1$H NMR (DMSO) $\delta$2.1 ppm (s, OCOC$\underline{H}_3$, 12H); $\delta$2.9 ppm and 3 ppm $$(s, -\underset{\underset{C\underline{H}_3}{|}}{N}-,\ 6\,H);$$

$\delta$3.5 ppm to 4,5 ppm (m, —N—C$\underline{H}_2$, C$\underline{H}_2$—O—, 8); $\delta$5.3 ppm (s, —C$\underline{H}$—2H); $\delta$5.6 ppm (s, N$\underline{H}_2$, 4H exchangeable with $D_2O$)

8) Preparation of 3,3'-bis-[5-(2-isopropyl) dioxan-1,3-yl] carbonylamino 5,5'-bis-[(N-methyl N-(2,3-diacetoxy propyl)carbamoyl]2,2', 4,4', 6,6'-hexaiodo diphenyl a) preparation of 5-(2-isopropyl dioxan-1,3-yl)carboxylic acid chloride 0.28 ml of $SOCl_2$ are added slowly to 0.6 g (0.0035 mole) of 5-(2-isopropyl dioxan-1,3-yl) carboxylic acid dissolved in 5.5 ml of dimethylacetamide. When the addition is complete, the solution is stirred for 5 h at room temperature b) After a portionwise addition of 0.68 g (0.0005 mole) of the compound obtained in 7) to the solution prepared in a), the crude reaction product is heated for 12 h at 45° C., then poured onto ice. The precipitate formed is filtered off, taken up in $CH_2Cl$, and washed with water. After being evaporated and taken up in ether, 0.7 g of beige crystals are obtained.

Yield: 83% TLC ($CH_2Cl_2$ 80/MeOH 20): RF=0.7

IR 1730 (OCO—$CH_3$); 1620 (CO—NH+CO—$NCH_3$)

$^1$H NMR (DMSO) $\delta$0.8 ppm $$(d, -\!\!\!\underset{CH_3}{\overset{CH_3}{\diagup}}\!\!\!\!\diagdown\ \ 12\,H)$$

$\delta$1.7 ppm $$(s, -C\underline{H}\!\!\diagdown^{\diagup})$$

2H); $\delta$2.1 ppm (s, OCOC$\underline{H}_3$, 12H); $\delta$2.9 ppm to 3.2 ppm (m, CO—C$\underline{H}$, N—$CH_3$, 8H), $\delta$3.4 ppm to 4.6 ppm (m, N—C$\underline{H}_2$—C$\underline{H}$—C$\underline{H}_2$, $$-\!\!\!\diagup\!\!\!\diagdown\underset{CH_2-O}{\overset{CH_2-O}{\diagup\diagdown}}\!\!\!\!\underline{CH},\ 20\,H$$

Preparation of 3,3'-bis-[5-(2-isopropyl) dioxan-1,3-yl]carbonylamino 5,5'-bis-[N-methyl N-(2,3-dihydroxypropyl)] carbamoyl 2,2', 4,4', 6,6'-hexaiodo diphenyl 0.5 g (0.3 mmole) of the compound obtained in 8) dissolved in 10 ml of MeOH containing 80 mg of $K_2CO_3$ in suspension are stirred for 24 hours at room temperature. After filtration, evaporation of the methanol and solidification in ether, 0.6 g of white crystals are obtained.

Yield>100% (presence of $K_2CO_3$)

IR 1620 (CO—N—$CH_3$+CO—NH);

$$3200-3500\ \ \underset{\underset{CH_2-OH}{|}}{-CH-OH}$$

TLC ($CH_2Cl_2$ 85/MeOH 15): $R_f$=0.3

$^1$H NMR (DMSO) $\delta$0.8 ppm $$(d, -\!\!\!\underset{C\underline{H}_3}{\overset{C\underline{H}_3}{\diagup}}\!\!\!\!\diagdown\ \ ,\ 12\,H)$$

$\delta$1.5 ppm to 1.8 ppm (m, —C$\underline{H}$, 2H); $\delta$2.9 ppm to 4.9 ppm (m, partially exchangeable with $D_2O$)

$$\underset{}{\overset{U}{\|}}\!\!-C-C\underline{H}\!\!\!\underset{CH_2-O}{\overset{CH_2-O}{\diagup\diagdown}}\!\!\!C\underline{H}-,$$

$$\underset{\underset{OH}{|}}{C\underline{H}_2-C\underline{H}-C\underline{H}_2-OH},\ 24\,H$$

11 ppm (s, —$\underline{H}$N—CO, 2 H).

Preparation of 3.3'-bis-[(3-hydroxy 2-hydroxymethyl) propionyl]amino 5,5'-bis-[N-methyl N-(2,3-dihydroxy-propyl)] carbamoyl 2,2', 4,4', 6,6'-hexaiodo diphenyl 0.5 mg (0.33 mmole) of the compound obtained in 9) are stirred in the presence of 13 ml of 5N hydrochloric acid for 6 h at room temperature. After evaporation, the residue obtained is purified by passage through $H^+$/$OH^-$resins, then by chromatography on silica.

After concentration and solidification in ether 0.3 g of white crystals are obtained.

Yield: 60% TLC ($CH_2Cl_2$ 60/MeOH 40): $R_f$=0.3 Purity with respect to iodine=99.5%

IR: 3200–3500

$$\underset{\underset{CH_2-OH;}{|}}{CH-OH}$$

1620 (CO—N—+CO—NH).

$^1$H NMR (DMSO): $\delta$2.6 ppm to 4 ppm (m, partially exchangeable with $D_2O$)

$$-N-C\underline{H}_2-C\underline{H}-C\underline{H}_2,\\\ \ \ |\\\ \ \ CH_3$$

$$-C-C\underline{H}\!\!\!\underset{CH_2-O\underline{H}}{\overset{CH_2-O\underline{H}}{\diagup\diagdown}}\ ,\ 30\,H\\\overset{\|}{O}$$

$\delta$4.4 ppm to 4.9 ppm $$(m, -\!\!\underset{OH\ \ OH}{\overset{|\ \ \ \ \ |}{C-CH_2}}\ ,$$

4H exchangeable with $D_2O$);

10 ppm (s, $\underline{H}$ N—CO)

$^{13}$C NMR: 38.35 ppm, s, N—CH$_3$, 50.57 ppm, s, N—CH$_2$ 59.99 ppm, s,

64.2 ppm, s, —CH$_2$—OH 69.92 ppm, s, CH—OH 94 to 105 ppm, m, C—I, 128 ppm,

143 to 156 ppm, m, ring C 173 ppm C=0

EXAMPLE 9

Preparation of 3,3'-bis-[(3-hydroxy 2-hydroxymethyl)propionyl]amino 5,5'-bis-[N-bis-(2,3-dihydroxy)propyl]carbamoyl 2,2', 4,4', 6,6'-hexaiodo diphenyl 1) Preparation of 3,3'-dinitro 5,5'-bis (2,3-dihydroxy propyl) carbamoyl diphenyl 0.9 g (2.7 mmoles) of the compound obtained in part 4) of Example 8 are added to a solution of 50 ml of SOCl$_2$ and 0.05 ml of dimethylformamide. The solution is heated at reflux for 6 h, then the SOCl$_2$ is distilled in a vacuum. The residual paste obtained is dissolved in 5 ml of CH$_2$Cl$_2$ and added dropwise at 5° C. to a solution of 1.8 g (0.011 mole) of 2,3-(N-2,3-dihydroxy propyl amino) propanediol and 1.53 ml (0.011 mole) of triethylamine dissolved in 10 ml of dimethylacetamide. When the addition is complete, the mixture is stirred for 12 h at room temperature. The triethylamine hydrochloride is removed by filtration and the solvents are evaporated. The residue is purified by chromatography on silica. After evaporation, 0.9 g of white crystals are obtained.

Yield=55% TLC (CH$_2$Cl$_2$ 60/MeOH 40): R$_f$=0.3
IR 3300–3500 (OH);

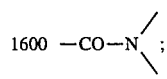

1520 NO$_2$
$^1$H NMR (DMSO) δ3 to 4 ppm (m, C$\underline{H}_2$—C$\underline{H}$—C$\underline{H}_2$, 20H); δ4.4 ppm to 5.2 ppm (m, CH—CH$_2$,
   |    |
   OH  OH 8H exchangeable with D$_2$O); δ8.3 ppm (s, 4H arom); δ8.6 ppm (s, 2H arom)

2) Preparation of 3,3'-diamino 5,5'-bis-/N-bis-(2,3-dihydroxy) propyl/carbamoyl diphenyl a) Reduction of the nitro groups:

0.8 g (1.27 mmole) of the compound obtained in 2) dissolved in 100 ml of MeOH are shaken in a 500 ml autoclave for 2 h30 at 40° C. under a hydrogen pressure of 6.10$^5$ Pa in the presence of 1 g of 10% aqueous Pd/C.

After removal of the catalyst by filtration and evaporation of the solvent a paste is obtained. TLC (CH$_2$Cl$_2$ 50/MeOH 50): R$_f$=0.05 b) Iodination by ICl:

0.84 ml (11 mmoles) of a 70% solution of ICl are added dropwise to the paste obtained in a) dissolved in 60 ml of a mixture MeOH/H$_2$O (50/50). When the addition is complete, the reaction mixture is heated at 60° C. for 4 h then left to stand at room temperature for 12 h. After evaporation of the brown solution to dryness, the residue solidifies in ethyl acetate. The dark beige crystals are filtered off, washed with carbon tetrachloride and petroleum ether. After drying, 0.7 g of beige crystals are obtained.

Yield=43% TLC (CH$_2$Cl$_2$ 65/MeOH 35): R$_f$=0.2 Purity with respect to iodine: 96%

$^1$H NMR (DMSO) δ3 to 4.2 ppm (m, partially exchangeable with D$_2$O)

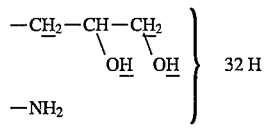

3) Preparation of 3,3'-diamino 5,5'-bis-[N-bis-(2,3-diacetoxy) propyl]carbamoyl 2,2', 4,4', 6,6'-hexaiodo diphenyl 0.7 ml of acetic anhydride are added dropwise to 0.3 g (0.23 mmole) of the compound contained in 2) dissolved in 5 ml of pyridine at 5° C. After being stirred for 18 h at room temperature, the reaction mixture is poured into ice-cold water acidified with 15 ml of 5N HCl. The precipitate formed is filtered off, then taken up in CH$_2$Cl$_2$. The organic phase is washed with water, then dried over MgSO$_4$. After evaporation and solidification in ether, 0.3 g of white crystals are obtained.

Yield: 80% Purity with respect to iodine=95% TLC (CH$_2$Cl$_2$ 85/MeOH 15): R$_f$=0.8

IR: 3300–3450: NH$_2$ 1720: —O—CO—CH$_3$

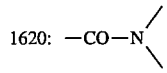

1580: —NH$_2$

4) Preparation of 3.3'-bis-[5-(2-isopropyl) dioxan-1,3-yl] carbonylamino 5,5'-bis-[N-bis-(2,3-diacetoxy)propyl]carbamoyl 2,2', 4,4', 6,6'-hexaiodo diphenyl)

a) Preparation of 5-(2-isopropyl dioxan-1,3-yl)carboxylic acid chloride:

0.112 ml of SOCl$_2$ are added slowly to 0.24 g (1.38 mmoles) of 5-(2-isopropyl dioxan-1,3-yl) carboxylic acid dissolved in 2.3 ml of dimethylacetamide at 0° C. When the addition is complete, the solution is stirred for 5 hours at room temperature.

b) After 0.3 g (0.2 mmole) of the compound obtained in 3) have been added portionwise to the solution obtained in a), the reaction mixture is heated for 12 h at 45° C., then poured onto ice.

The precipitate formed is filtered off, taken up in CH$_2$Cl$_2$ and washed with water. After being evaporated and taken up in ether, 0.2 g of beige crystals are obtained.

Yield: 52%
IR: 1730 (OCOCH$_3$);

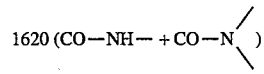

TLC (CH$_2$Cl$_2$ 95/MeOH 5); R$_f$=0.45

5) Preparation of 3,3'-bis-[5-(2-isopropyl) dioxan-1,3-yl] carbonylamino 5,5'-bis-[N-bis-(2,3-dihydroxy) propyl]carbamoyl 2,2', 4,4', 6,6'-hexaiodo diphenyl 0.2 g (0.1 mole) of the compound obtained in 4) and 50 mg of $K_2CO_3$ are dissolved in 5 ml of MeOH and stirred for 18 h at room temperature. After filtration and evaporation of the methanol, 200 mg of white crystals are obtained.

6) Preparation of 3,3'-bis-[(3-hydroxy 2-hydroxymethyl-)propionyl]amino 5,5'-bis-[N-bis(2,3-dihydroxy)-propyl] carbamoyl 2,2', 4,4', 6,6'- hexaiodo diphenyl 0.2 g of the compound obtained in 5) are stirred in the presence of 5 ml of 5N HCl for 6 h at room temperature. After evaporation, the residue obtained is purified by passage through $H^+/OH^-$ resins and by crystallization from ether. 100 mg of white crystals are obtained.

Yield=50% (overall for the steps 5) and 6) Purity with respect to iodine=93% TLC ($CH_2Cl_2$ 20/MeOH 80): 2 spots joined together: $R_f$=0.8

IR: 3200–3500

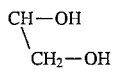

1600

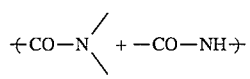

$^1$H NMR (DMSO) δ3 to 5.1 ppm (m, partially exchangeable with $D_2O$)

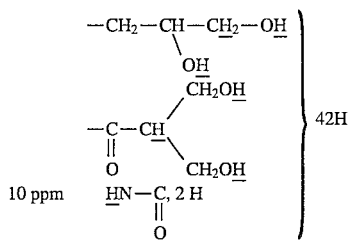

EXAMPLE 10

Preparation of the compound of formula:

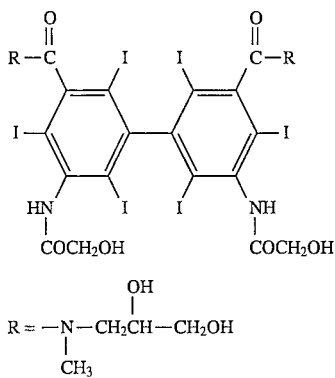

1 - Preparation of the compound of formula:

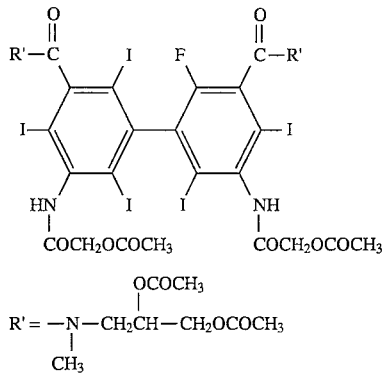

1.4 g (0.01 mole) of $Cl-CO-CH_2OCOCH_3$ are added dropwise to 5.5 g (0.0040 mole) of the compound obtained in example 8-7 dissolved in 15 ml of DMAC. The solution obtained is stirred at 50° C. for 16 h, then poured onto ice. The precipitate obtained is filtered off, washed with $H_2O$ then dried. 3.4 g of white crystals are obtained.

Yield: 55% TLC (ethyl acetate): $R_f$:0.3

I.R.: 1730 ($OCO-CH_3$) 1620 ($CO-NH+CO-N-CH_3$)

$^1$H NMR (DMSO) δ1.9 ppm - 2.1 ppm (2s, $OCOCH_3$, 18H); δ2.8 ppm

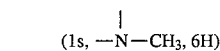

δ3.5 ppm to 4.5 ppm (m, $CH_2-CH-CH_2$, 8H) δ4.7 ppm (s, $CO-CH_2-O$, 4H) δ5.3 ppm (m, $CH_2-CH-CH_2$, 2H) δ10.3 ppm (s, $NH-CO$, 2H exchangeable with $D_2O$)

2-Preparation of the compound of formula:

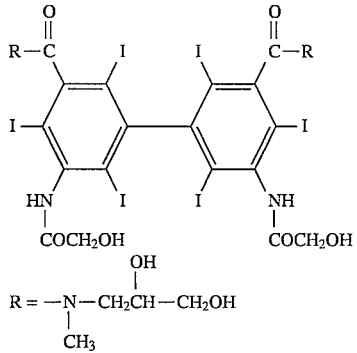

2.5 g (0.00153 mole) of the compound obtained in 1) dissolved in 100 ml of MeOH and 1.3 g (0.01 mole) of $K_2CO_3$ are stirred for 48 h at room temperature. After filtration and evaporation of the methanol, the residue is dissolved in 100 ml of water, then passed through a $H^+$resin. After evaporation, the product obtained is purified by chromatography on silica. After evaporation and solidification in ether, 1.6 g of white crystals are obtained.

Yield: 76% TLC: silica; $CH_2Cl_2$/MeOH: 70/30; $R_f$:0.4 Purity with respect to iodine=99.5%

I.R. ($cm^{-1}$) 1600 ($CO-NH+CO-N-CH_3$); 3200–3500

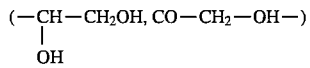

$^1$H NMR (DMSO): δ2.8 ppm (1s, $-N-CH_3$, 6H); δ3 ppm to 3.9 ppm (m, $CH_2-CH-CH_2$, 10H); δ4 ppm (1s, —CO—CH₂—OH, 4H); δ5.8 ppm to 4.1 ppm

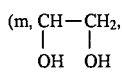

CO—CH₂—OH, 6H exchangeable with D₂O); δ9.8 ppm (1s, NH—CO—, 2H exchangeable with D₂O).

¹³C NMR: 38.35 ppm s, —N—CH₃ 50 ppm s, —N—CH₂ 61 ppm s, —CO—CH₂—OH 63 ppm s, —CH₂—CH₂—OH 69.5 ppm s,

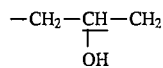

98 to 105 ppm, C—I (ring) 144 ppm s, C—NH (ring) 148.5 ppm s, C—C (diphenyl) 155 ppm s, C—CO(ring) 170 ppm s, NH—CO—CH₂+C—CO—N

EXAMPLE 11

Preparation of the compound of formula:

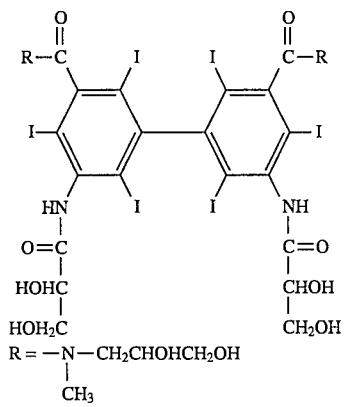

I - Preparation of the compound of formula:

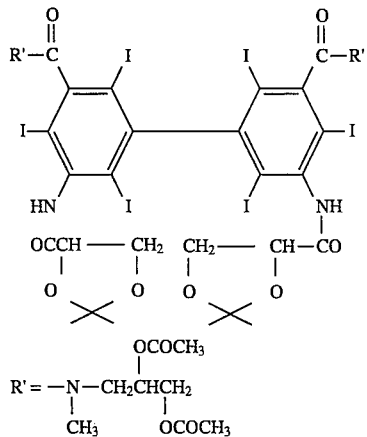

a) Preparation of the compound of formula:

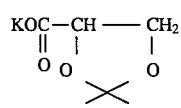

An aqueous solution of 294 g (1.75 mole) of KMnO₄ is added dropwise to an aqueous solution of 150 g (1.14 mole) of Solketal® (commercially available from the Janssen company (Pantin)) and 69.4 g (1.23 mole) of potassium, the temperature being maintained at 4°–9° C.

The reaction mixture is stirred overnight at room temperature. After filtration, adjustment of the pH of the solution to 9 and concentration to dryness, the residue is taken up in ethanol. The mineral salts are filtered off and the ethanolic phase is concentrated to dryness.

Yield: 75% (potassium salt) b) Preparation of the compound of formula:

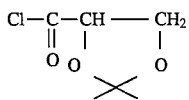

1.15 ml of oxalyl chloride are added dropwise to 2.2 g (0.012 mole) of the product obtained in a) above suspended in 12 ml of anhydrous ether at a temperature of 0° C. The mixture is stirred for two hours at 0° C., then for 18 hours at room temperature.

After removal of the KCl by filtration, the solution is evaporated at 20° C. in a vacuum.

c) The solution prepared in b) above is added dropwise to 2.7 g (0.002 mole) of the compound obtained in example 8-7) dissolved in 10 ml of DMAC. The mixture obtained is stirred for 17 hours at room temperature, then poured into ether. The crystals formed are filtered off and dried. 3 g of beige crystals are obtained in a yield of 90%. TLC (ethyl acetate): R_f=0.75

2 - Preparation of the compound of formula:

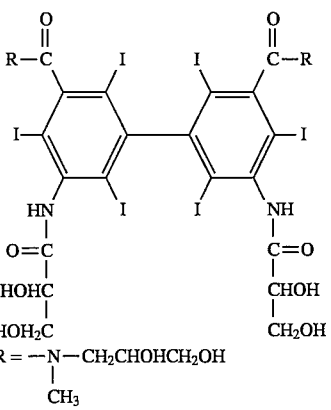

3 g (0.0018 mole) of the compound obtained in the preceding step in 150 ml of methanol and 1.8 g (0.015 mole) of K₂CO₃ are stirred for 48 hours at room temperature. After filtration and evaporation of the methanol, the residue is dissolved in an aqueous solution at pH3. The solution is stirred for one hour, passed through H⁺and OH⁻resins, then purified by chromatography on silica. After evaporation and solidification in ether, 1.2 g of white crystals are obtained (Yield=46%) TLC (CH₂Cl/MeOH:50/50) R_f:0.6 Purity with respect to iodine: 99%

IR: 1600 (CO—N—CH₃+CO—NH—); 3200–3500

CH—CH₂OH, —CH—CH₂OH
|                |
OH              OH

¹H NMR (DMSO) δ2.8 ppm (1s, —N—CH₃, 6H); δ3 to 4.1 ppm (m, CH₂—CH—CH₂, CH—CH₂ 16H); δ4.55 to 4.75 ppm

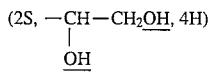

δ5.65 ppm,

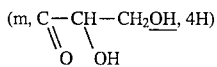

δ9.7 ppm (m, NH—CO, 2H)

$^{13}$C NMR (DMSO) 38.35 ppm (s, —N—CH$_3$); 50 ppm (s, —N—CH$_2$) 64 ppm (s, —CH$_2$—OH) 70 and 73.5 ppm (2s, CH—OH) 95 to 105 ppm (m, C—I) 143 to 155 ppm (3s, C—C diphenyl; C—N of the ring; C—C=O) 170 ppm

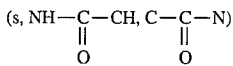

EXAMPLE 12

Preparation of the compound of formula:

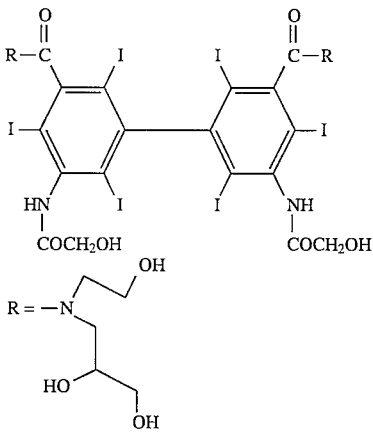

1 -Preparation of the compound of formula:

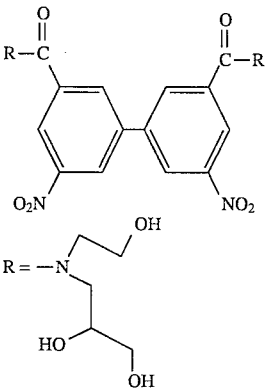

a) Synthesis of the compound of formula:

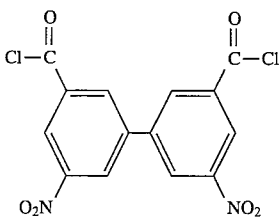

9.9 g (0.03 mole) of the compound obtained in example 8-4) are added to a solution of 100 ml of SOCl$_2$ and 0.1 ml of dimethyl-formamide. The solution is heated at reflux for 5 h. After evaporation of the SOCl$_2$, the paste obtained is dissolved in dioxan.

b) amidation

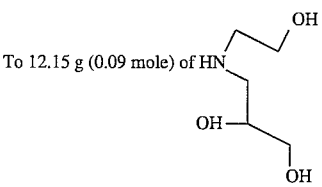

To 12.15 g (0.09 mole) of obtained according to the procedure described in WO-9109007 and 21.4 ml (0.09 mole) of tributylamine dissolved by heating in 100 ml of dioxan is added dropwise at 80° C. to the product obtained in a). The mixture is stirred overnight at room temperature. The supernatant is decanted and the viscous residue is washed with CH$_2$Cl$_2$, then with ether. 20 g of the title compound are obtained. TLC (CH$_2$Cl$_2$/MeOH:75/25) R$_f$=0.7

IR: 3100–3500 (OH); 1610,

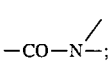

1520, NO$_2$ $^1$H NMR (DMSO) δ3 to 3.5 ppm

δ3.9 ppm

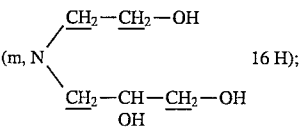

δ4.5 to 5 ppm

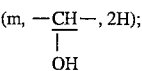

6H exchangeable with D$_2$O); δ8.3 ppm 1d δ8.6 ppm 1s CH aromatic, 6H $^{13}$C NMR (DMSO) 48 ppm (2s, N—CH$_2$—CH$_2$OH) 52 ppm

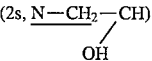

58 ppm (2s, CH$_2$—CH$_2$OH) 63 ppm (2s, CH—CH$_2$OH) 69 ppm

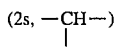
(2s, —CH—)

|         |     |              |
|---------|-----|--------------|
| 122 ppm | (1s |              |
| 133 ppm | (1s | } C-C aromatic |
| 140 ppm | (2s |              |
| 149 ppm | (1s |              |

168 ppm 1s, —CO—

2 - Preparation of the compound of formula:

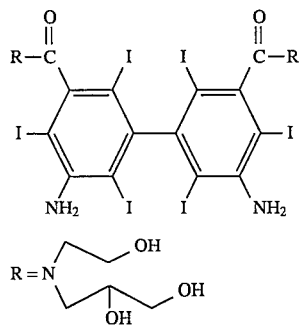

a) Reduction of the nitro groups:

0.03 mole of the compound obtained in 1) dissolved in 300 ml of methanol are shaken in a 500 ml autoclave in the presence of 1 g of 10% Pd/C for 5 h at 50° C. under a hydrogen pressure of 6.10$^5$ Pa. After removal of the catalyst by filtration and evaporation of the solvent a paste is obtained. TLC (CH$_2$Cl$_2$/MeOH 50/50) R$_f$=0.2 b) Iodination by ICl:

53 ml (0.3 mole) of a 70% solution of ICl are added dropwise to the paste obtained in a) dissolved in 500 ml of methanol. The reaction mixture is heated at 60° C. for 12 h. After being cooled, the solution is poured into a mixture of ice and water. The precipitate obtained is filtered off and washed with a dilute aqueous bisulfite solution.

The product thus obtained is redissolved in methanol (V-300 ml) and 10.6 ml (0.06 mole) of a 70% solution of ICl are added dropwise. The mixture is stirred for 12 h at 60° C., then poured onto ice, and the precipitate formed is washed by a dilute aqueous bisulfite solution. The product is taken up in ether, then dried. 23 g of beige crystals are obtained.

Yield: 63% Purity with respect to iodine: 98% TLC (CH$_2$Cl$_2$/MeOH: 75/25): R$_f$=0.4

IR: 3100–3500 (OH); 1580 NH$_2$,

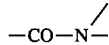
—CO—N $^1$H NMR (DMSO) δ3.1 ppm to 4 ppm: (m, CH$_2$—CH$_2$—, 8H, CH$_2$—CH—CH$_2$, 10H); δ4.4 ppm to 4.9 ppm:

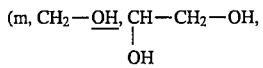
(m, CH$_2$—OH, CH—CH$_2$—OH, OH)

6H exchangeable with D$_2$O δ5.5 ppm (s, NH$_2$ 4H exchangeable with D$_2$O)

3 - Preparation of the compound of formula:

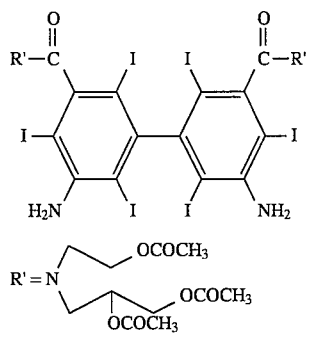

30 ml of acetic anhydride are added dropwise to 23 g (0.0182 mole) of the compound obtained in 2) dissolved in 280 ml of pyridine at 5° C. After the reaction mixture has been stirred for 18 h at room temperature, the reaction medium is poured into acidified, ice-cold water. The precipitate water is filtered off, then taken up in CH$_2$Cl$_2$. The organic phase is washed with water, dried over MgSO$_4$ and purified by chromatography on silica.

After evaporation, 11 g of white crystals are obtained.

Yield: 50% TLC (ethyl acetate/heptane: 9/1) R$_f$=0.6
Purity with respect to iodine: 97%

$^1$H NMR (DMSO) δ2 ppm (m, O—CO—CH$_3$, 18H); δ3.1 ppm to 4.1 ppm (m, CH$_2$—CH$_2$, 8H, CH$_2$—CH—CH$_2$, 8H); δ5.1 ppm to 5.4 ppm (s, NH$_2$, 4H) (m, CH$_2$—CH—CH$_2$, 2H).

4 - Preparation of the compound of formula:

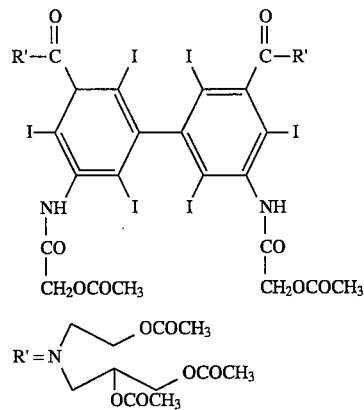

a) Preparation of Cl—CO—CH$_2$—OCOCH$_3$: 88 g (0.745 mole) of COOH—CH$_2$OCOCH$_3$ are added to a solution of 200 ml of SOCl$_2$, then heated at reflux for 5 hours.

After evaporation of the SOCl$_2$, 70 g of product are recovered by distillation.

Yield: 70% b) Acylation:

10 g (0.073 mole) of the acid chloride obtained in 4a) are added dropwise to 22 g (0.0145 mole) of the compound obtained in 3) dissolved in 150 ml of anhydrous DMAC. The mixture is heated at 60° C. for 5 h, then poured onto ice. The precipitate formed is taken up in CH$_2$Cl$_2$ and washed with water, purified by chromatography on silica then solidified on trituration with isopropyl ether. 14 g of white crystals are obtained.

Yield: 60% Purity with respect to iodine: 99% TLC (ethyl acetate) R$_f$0.8

$^1$H NMR (DMSO): δ1.9 ppm to 2.2 ppm (m, O—CO—CH$_3$, 18H); δ6 3.3 ppm to 4.5 ppm (m, CH$_2$—CH$_2$, 16H)

$CH_2$—CH—$CH_2$ δ4.7 ppm (s, CO—$CH_2$—O—, 4H); δ5.4 ppm (s, $CH_2$—CH—$CH_2$, 2H); δ10.3 ppm (s, NH—CO—, 2H exchangeable with $D_2O$)

5 - Preparation of the compound of formula:

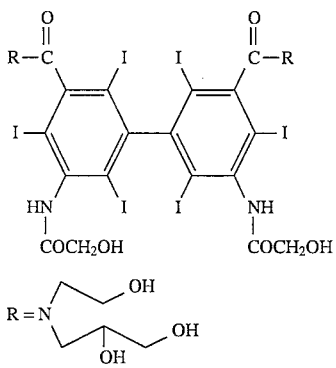

14 g (0.00816 mole) of the compound obtained in 4b) and 1.4 g of $K_2CO_3$ suspended in 140 ml of methanol are stirred for 18 h at room temperature. After filtration and evaporation white crystals are obtained, which are then purified on a $H^+$resin and by chromatography on silica. 8 g of product are obtained.

Yield: 80% TLC ($CH_2Cl_2$/MeOH 60/40): $R_f$=0.4

IR: 3100–3500—R—OH; 1590—NH—CO—+—CO—N—

$^1H$ NMR (DMSO) 3.1 ppm to 3.9 ppm (m, $CH_2$—$CH_2$, $CH_2$—CH—$CH_2$, 18H) 4 ppm (1s, —CO—$CH_2$—OH, 4H); 4.5 to 4.9 ppm

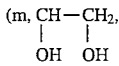

$CH_2$—$CH_2$—OH, 6H exchangeable with $D_2O$); 5.5 ppm (ppm (1s, COCH$_2$OH, 2H); 9.8 ppm (1s, —NH—CO, 2H exchangeable with $D_2O$)

$^{13}C$ NMR (DMSO)

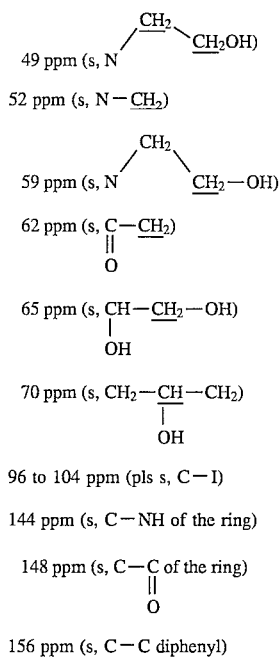

-continued 171 ppm (pls s C—N)
               ‖
               O
   NH—C—)
      ‖
      O

EXAMPLE 13

Preparation of the compound of formula:

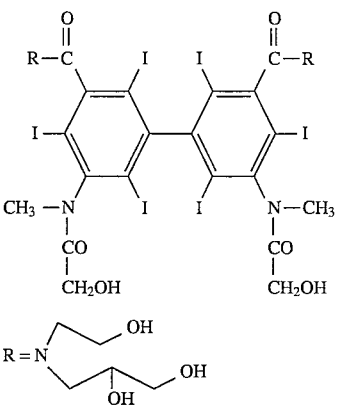

1 g (0.000725 mole) of the compound obtained in example 12-5) is dissolved in 6 ml of anhydrous methanol containing 0.0015 mole of sodium methylate. The reaction mixture is stirred for 1 hour, then 0.17 ml (0.002 mole) of methyl iodide are added dropwise and the solution is heated at 35°–40° C. for 3 hours. After evaporation of the solvent, the residue solidifies in ether, is washed with acetone and purified by chromatography on silica. 600 mg of white crystals are obtained.

Yield: 70% Purity with respect to iodine: 99% TLC ($CH_2Cl_2$/MeOH/$NH_4OH$: 60/30/10): $R_f$:0.3

EXAMPLE 14

Preparation of the compound of formula:

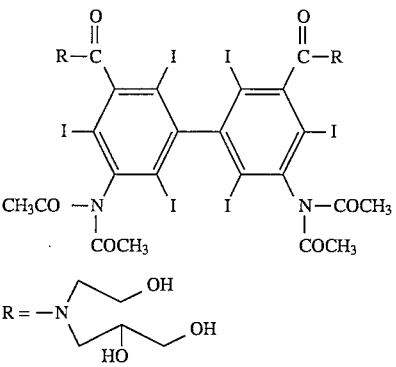

7.1 g (4.7 mmoles) of the compound obtained in example 12-2b) are added to a solution of acetyl chloride (1.2 ml) (0.0165 mole) in 80 ml of DMAC. The reaction mixture is heated at 60° C. for 72 h. After being allowed to cool to room temperature, the reaction mixture is precipitated by means of an ice+water mixture.

The crude product (7.2 g; yield 96%) obtained after filtration and solidification in heptane is purified on a column of silica. 5.8 g of product are obtained.

Yield: 77% TLC (CH₂Cl₂/MeOH 90/10) R_f:0.7 Purity with respect to iodine: 98.4% HPLC purity: 97% Lichrosphere C₁₈, 5μ, 25 cm CH₃CN 80,50 H₂O 20,50

¹H NMR (DMSO): 200 MHz; δ5.2 to 5.4 ppm (m, CH 2H); δ4 to 4.4 ppm (m, C$\underline{H}_2$—OAc 8H); δ3.7 to 4 ppm (m, CONC$\underline{H}_2$C$\underline{H}_2$OAc 8H); δ2.15 to 2.4 ppm

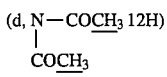

δ1.8 to 2.2 ppm (s, —OCOCH₃ 18H).

EXAMPLE 15

Preparation of the compound of formula:

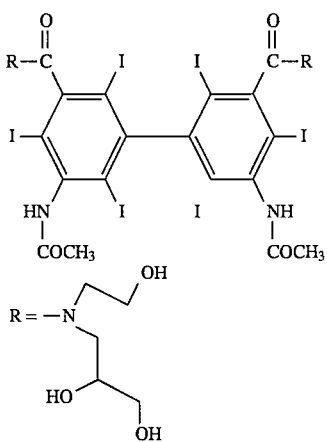

7.5 g (4.45 mmoles) of the compound obtained in example 14 are added to a 5N solution of sodium hydroxide (5 ml) in a methanol-water mixture (30/15). The reaction mixture is stirred at 50° C. for 2 h and at room temperature overnight.

After concentration and purification of the reaction medium on SiO₂, desalting is performed by passages through H⁺and OH⁻resins. After concentration of the aqueous phase, 3.2 g of a white solid are obtained (yield 54%) Purity with respect to iodine: 98.5% HPLC purity: 99.9% Lichrosphere C₁₈, 25 cm, 5μ H₂O 50 CH₃CN 50

¹H NMR (DMSO) δ20 ppm, s,—NH—,2H; δ4,6–4.9 ppm, m,—OH, 6H; δ4 ppm, s, —CH—, 2H ; δ3.2 to 3.8 ppm, m,

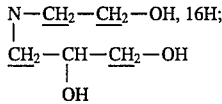

δ2 ppm, s,NHCOCH₃, 6H

EXAMPLE 16

Preparation of the compound of formula:

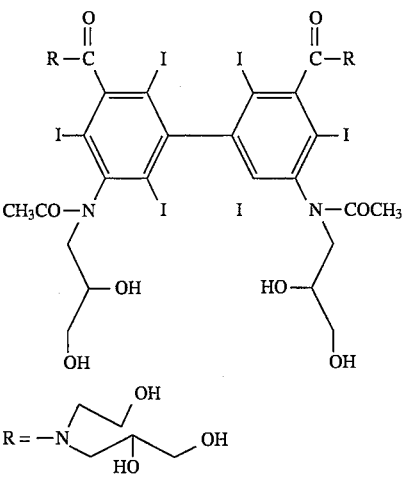

404 mg (3 mmoles) of the product prepared in example 15 are dissolved in 3 ml of methanol.

1.7 ml (8.4 mmoles) of a 5N solution of sodium methylate and 1.25 ml (15 mmoles) of 3-chloro-1,2-propanediol are simultaneously added dropwise.

The reaction mixture is stirred for 7 days at 35° C.

After neutralization with 1N HCl and desalting on H⁺and OH⁻resins, the title product is obtained. TLC (CH₂Cl₂/MeOH 40/60): R_f:0.3 HPLC purity: 97.7% Column R sil NH₂ 25F, 5 μm, 25 cm; CH₃CN: 75; H₂O: 25.

We claim:

1. Tetra-iodinated compounds of general formula:

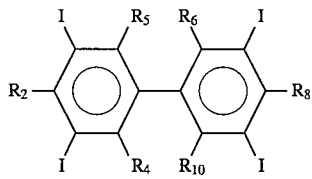

in which $R_2$, $R_4$, $R_5$, $R_6$, $R_8$ and $R_{10}$ are selected from:

a) a group of formula

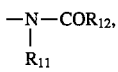

in which $R_{11}$ and $R_{12}$, identical or different, represent a hydrogen atom, a linear or branched $C_1$-$C_6$ alkyl group, a linear or branched hydroxy- or polyhydroxy-$C_1$-$C_6$ alkyl group, optionally having in addition one or more $C_1$-$C_6$ alkoxy groups, a linear or branched $C_1$-$C_6$-alkoxy-$C_1$-$C_6$ alkyl group or a linear or branched hydroxy- or polyhydroxy-$C_1$-$C_6$ alkoxy-$C_1$-$C_6$ alkyl group having from two to five —OH groups;

b) a group formula

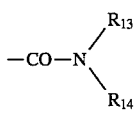

in which groups

R$_{13}$ and R$_{14}$, identical or different, represent a hydrogen atom, a linear or branched C$_1$–C$_6$ alkyl group, a linear or branched C$_1$–C$_6$ hydroxy- or polyhydroxyalkyl group, optional having in addition one or more C$_1$–C$_6$ alkoxy groups, a linear or branched C$_1$–C$_6$ alkoxy-C$_1$–C$_6$ alkyl group or a linear or branched hydroxy- or polyhydroxy-C$_1$–C$_6$-alkoxy-C$_1$–C$_6$ alkyl group having from two to five —OH groups.

2. Hexa-iodinated compounds of general formula:

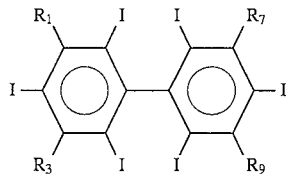     III in which R$_1$, R$_3$, R$_7$, R$_9$ are selected from:

a) a group of formula —NR$_{11}$—COR$_{12}$ in which R$_{11}$ and R$_{12}$, identical or different, represent a hydrogen atom, a linear or branched C$_1$–C$_6$ alkyl group, a linear or branched hydroxy- or polyhydroxy-C$_1$–C$_6$ alkyl group, optionally having in addition one or more C$_1$–C$_6$ alkoxy groups, a linear or branched C$_1$–C$_6$-alkoxy-C$_1$–C$_6$ alkyl group or a linear or branched hydroxy- or polyhydroxy-C$_1$–C$_6$alkoxy-C$_1$–C$_6$ alkyl group having from two to five —OH groups;

b) a group formula

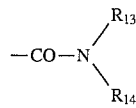

in which groups

R$_{13}$ and R$_{14}$, identical or different, represent a hydrogen atom, a linear or branched C$_1$–C$_6$ alkyl group, a linear or branched C$_1$–C$_6$ hydroxy- or polyhydroxyalkyl group, optionally having in addition one or more C$_1$–C$_6$ alkoxy groups, a linear or branched C$_1$–C$_6$ alkoxy-C$_1$–C$_6$ alkyl group or a linear or branched hydroxy- or polyhydroxy-C$_1$–C$_6$-alkoxy-C$_1$–C$_6$ alkyl group having from two to five —OH groups.

3. Compounds according to claim 1 selected from the compounds of formula II in which R$_2$ and R$_8$ represent the group —CO—NH—CH$_2$—CHOH—CH$_2$—OH and R$_4$, R$_5$, R$_6$ and R$_{10}$ represent the group —NH—CO—CHOH—CH$_3$, R$_2$ and R$_8$ represent the group —NH—CO—CH$_2$OH and R$_4$, R$_5$, R$_6$ and R$_{10}$ represent the group —CO—NH—CH$_2$—CH$_2$OH, R$_2$ and R$_8$ represent the group

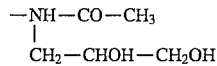

and R$_4$, R$_5$, R$_6$ and R$_{10}$ represent the group —CO—NH—CH$_2$—CH$_2$OH and R$_2$ and R$_8$ represent the group —CO—NH—CH$_2$—CHOH—CH$_2$OH and R$_4$, R$_5$, R$_6$ and R$_{10}$ represent the group —CO—NH—CH$_2$—CHOH—CH$_2$OH.

4. Compound of formula II according to claim 1 in which R$_2$, R$_5$, R$_6$ and R$_8$ represent the group —CO—NH—CH$_2$—CHOH—CH$_2$OH and R$_4$ and R$_{10}$ represent the group —NH—CO—CH$_2$OH.

5. Compound of formula II according to claim 1 in which R$_2$, R$_4$, R$_5$, R$_6$, R$_8$ and R$_{10}$ represent the group —NH—CO—CHOH—CH$_3$.

6. Compound of formula II according to claim 1 in which R$_2$, R$_4$, R$_5$, R$_6$ and R$_8$ represent the group —CO—NH—CH$_2$—CH$_2$OH and R$_3$ and R$_{10}$ represent the group —NH—CO—CHOH—CH$_3$.

7. Compound according to claim 2 selected from the compounds of formula III in which R$_1$ and R$_7$ represent the group —NH—CO—CH(CH$_2$OH)$_2$ and R$_3$ and R$_9$ represent the group —CO—N(CH$_3$)—CH$_2$—CHOH—CH$_2$OH, R$_1$ and R$_7$ represent the group —NH—CO—CH—(CH$_2$OH)$_2$ and R$_3$ and R$_9$ represent the group —CO—N—(CH$_2$—CHOH—CH$_2$OH)$_2$, R$_1$ and R$_7$ represent the group —NH-COCH—CH$_2$OH and R$_3$ and R$_9$ represent the group —CO—N(CH$_3$)—CH$_2$—CHOH—CH$_2$OH, R$_1$ and R$_7$ represent the group —NH—CO—CH$_2$OH and R$_3$ and R$_9$ represent the group —CO—N(CH$_3$)—CH$_2$—CHOH—CH$_2$OH, R$_1$ and R$_7$ represent the group —NH—CO—CH$_2$OH and R$_3$ and R$_9$ represent the group

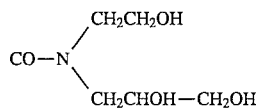

R$_1$ and R$_7$ represent the group —N(CH$_3$)—CO—CH$_2$OH and R$_3$ and R$_9$ represent the group

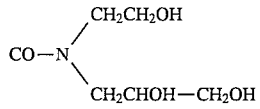

R$_1$ and R$_7$ represent the group —NH—CO—CH$_3$ and R$_3$ and R$_9$ represent the group

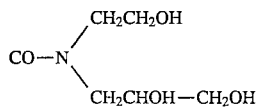

R$_1$ and R$_7$ represent the group

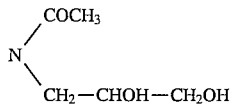

and R$_3$ and R$_9$ represent the group

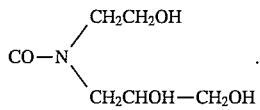

* * * * *